(12) United States Patent
Sawant et al.

(10) Patent No.: US 10,898,157 B2
(45) Date of Patent: Jan. 26, 2021

(54) DEFORMABLE LUNG MODEL APPARATUS

(71) Applicant: University of Maryland, Baltimore, Baltimore, MD (US)

(72) Inventors: Amit Sawant, Columbia, MD (US); Maida Ranjbar, Baltimore, MD (US); Pouya Sabouri, Baltimore, MD (US); Carlo Repetto, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 36 days.

(21) Appl. No.: 16/269,044

(22) Filed: Feb. 6, 2019

(65) Prior Publication Data

US 2019/0239846 A1 Aug. 8, 2019

Related U.S. Application Data

(60) Provisional application No. 62/626,883, filed on Feb. 6, 2018.

(51) Int. Cl.
*A61B 6/00* (2006.01)
*G09B 23/28* (2006.01)
*G09B 23/32* (2006.01)
*A61N 5/10* (2006.01)

(52) U.S. Cl.
CPC .......... *A61B 6/583* (2013.01); *A61N 5/1075* (2013.01); *G09B 23/288* (2013.01); *G09B 23/32* (2013.01); *A61N 2005/1076* (2013.01)

(58) Field of Classification Search
CPC .......... A61B 6/583; A61N 2005/1076; A61N 5/1075; G09B 23/288; G09B 23/32
See application file for complete search history.

(56) References Cited

U.S. PATENT DOCUMENTS

| 2008/0298540 | A1* | 12/2008 | Serban | G09B 23/32 |
| | | | | 378/18 |
| 2010/0137709 | A1* | 6/2010 | Gardner | G09B 23/286 |
| | | | | 600/426 |
| 2014/0243579 | A1* | 8/2014 | Roeske | A61B 6/485 |
| | | | | 600/1 |

(Continued)

OTHER PUBLICATIONS

Bortfeld, Thomas et al. 2004. "Effects of Motion on the Total Dose Distribution." Seminars in Radiation Oncology. vol. 14, No. 1 41-51.

(Continued)

*Primary Examiner* — David P Porta
*Assistant Examiner* — Fani Boosalis
(74) *Attorney, Agent, or Firm* — Olive Law Group, PLLC

(57) ABSTRACT

A lung motion phantom device and method of operation. The device has a body having an outer shell and a lung insert, a first actuator connected to a first drive linkage for driving a first displacement of an internal volume of the lung insert and an outer surface of the outer shell in a first direction, a second actuator connected to a second drive linkage for driving a second displacement of the internal volume of the lung insert and the outer surface of the outer shell in a second direction different than the first direction, and a controller programmed to control the first and second actuators such that the first and second displacements simulate movement of an external surface and an interior of a thoracic region of a patient.

20 Claims, 24 Drawing Sheets

(56) References Cited

U.S. PATENT DOCUMENTS

2017/0207726 A1* 7/2017 Barberi .................. H01L 41/09

OTHER PUBLICATIONS

Cai, Jing et al. 2007. "Estimation of error in maximal intensity projection-based internal target volume of lung tumors: a simulation and comparison study using dynamic magnetic resonance imaging." Int. J. Radiation Oncology Biol. Phys. vol. 69, No. 3. 895-902.

Chang, Jina et al. 2010. "Development of a deformable lung phantom for the evaluation of deformable registration." Journal of Applied Clinical Medical Physics. vol. 11, No. 1. 281-286.

Cherpak, Amanda et al. 2011. "4D dose-position verification in radiation therapy using the RADPOS system in a deformable lung phantom." Med. Phys. vol. 38 (1). 179-187.

Cheung, Yam and Sawant, Amit. 2015. "An externally and internally deformable, programmable lung motion phantom." Med. Phys. vol. 42 (5). 2585-2593.

Court, Laurence E. et al. 2010. "Use of a realistic breathing lung phantom to evaluate dose delivery errors" vol. 37, 11. 5850-5857.

Dawson, Laura A. et al. 2001. "The reproductibility of organ position using active breathing control (ABC) during liver radiotherapy." Int. J. Radiation Oncology Biol. Phys., vol. 51. 1410-1421.

Ford, E. C. et al. 2002. "Evaluation of respiratory movement during gated radiotherapy using film and electronic portal imaging." Int. J. Radiation Oncology Biol. Phys., vol. 52, No. 2. 522-531.

James, Sara St. et al. 2012. "Quantifying ITV instabilities arising frm 4DCT: a simulation study using patient data." Phys. Med. Biol. vol. 57. L1-L7.

Kashani, Rojano et al. 2007. "Technical note: A deformable phantom for dynamic modeling in radiation therapy." Med. Phys. vol. 34 (1). 199-201.

Keall, P. J. et al. 2001. "Motion adaptive x-ray therapy: a feasibility study." vol. 46. 1-10.

Li, Ruijiang et al. 2011. "On a PCA-based lung motion model." Phys. Med. Biol. vol. 56. 6009-6030.

Lujan, Anthony E. et al. 1999. "A method for incorporating organ motion due to breathing into 3D dose calculations." Med. Phys. vol. 26 (5). 715-720.

Malinowski, K. et al. 2007. "Development of the 4DPhantom for patient-specific, end-to-end radiation therapy QA." Physics of Medical Imaging. vol. 6510.

Malinowski, Kathleen et al. 2012. "Incidence of changes in respiration-induced tumor motion and its relationship with respiratory surrogates during individual treatment fractions." vol. 82, No. 5. 1665-1673.

Murphy, Martin J and Dieterich, Sonja. 2006. "Comparative performance of linear and nonlinear neural networks to predict irregular breathing." Phys. Med. Biol. vol. 51. 5903-5914.

Murphy, Martin J. 2007. "The management of imaging dose during image-guided radiotherapy: Report of the AAPM Task Group 75." Med. Phys. 34 (10). 4041-4063.

Nehmeh, S. A. et al. 2004. "Quantitation or respiratory motion during 4D-PET/CT acquisition." Medical Physics. vol. 31, 6. 1333-1338.

Neicu, Toni et al. 2003. "Synchronized moving aperture radiation therapy (SMART): average tumour trajectory for lung patients." vol. 48. 587-598.

Nioutsikou, Elena et al. 2006. "Quantifying the effect of respiratory motion on lung tumour dosimetry with the aid of a breathing phantom with deforming lungs." Phys. Med. Biol. vol. 51. 3359-3374.

Niu, Carolyn J. et al. 2012. "A novel technique to enable experimental validation of deformable dose accumulation." Med. Phys. vol. 39 (2). 765-776.

Pan, Tinsu. 2004. "4D-CT imaging of a volume influenced by respiratory motion on multi-slice CT." Med. Phys. vol. 31 (2). 333-340.

Persson, Gitte Fredberg et al. 2010. "Ddeviations in delineated GTV caused by artefacts in 4DCT." Radiotherapy and Oncology. vol. 96. 61-66.

Persson, Gitte Fredberg et al. 2011. "Artifacts in conventional computed tomography (CT) and free breathing four-dimensional CT induce uncertainty in gross tumor volume determination." Int. J. Radiation Oncology Biol. Phys., vol. 80, No. 5. 1573-1580.

Remmert, G. et al. 2007. "Four-dimensional magnetic resonance imaging for the determination of tumour movement and its evaluation using a dynamic porcine lung phantom." Phys. Med. Biol. vol. 52. N401-N415.

Sarker, Joyatee et al. 2010. "Variations in tumor size and position due to irregular breathing in 4D-CT: a simulation study." Med. Phys. vol. 37 (3). 1254-1260.

Seppenwoolde, Yvette et al. 2002. "Precise and real-time measurement of 3D tumor motion in lung due to breathing and heartbeat, measured during radiotherapy." Int. J. Radiation Oncology Biol. Phys., vol. 53, No. 4. 822-834.

Seppenwoolde, Yvette et al. 2007. "Accuracy of tumor motion compensation algorithm from a robotic respiratory tracking system: A simulation study." Med. Phys. vol. 34 (7). 2774-2784.

Serban, Monica et al. 2008. "A deformable phantom for 4D radiotherapy verification: Design and image registration evaluation." Med. Phys. vol. 35 (3). 1094-1102.

Sharp, Gregory C. et al. 2004. "Prediction of respiratory tumour motion for real-time image-guided therapy." Phys. Med. Biol. vol. 49. 425-440.

Starkschall, George et al. 2007. "Quantitative assessment of four-dimensional computed tomography image acquisition quality." Journal of Applied Clinical Medical Physics. vol. 8., No. 3. 1-20.

Suh, Yelin et al. 2008. "An analysis of thoracic and abdominal tumour motion for stereotactic body radiotherapy patients." Phys. Med. Biol. vol. 53. 3623-3640.

Tang, Jonathan et al. 2004. "Respiratory motion tracking of skin and liver in swine for Cyberknife motion compensation." Medical Imaging.

Vedam, S.S. et al. 2003. "Acquiring a four-dimensional computed tomography dataset using an external respiratory signal." Phys. Med. Biol. vol. 48. 45-62.

Yang, Deshan et al. 2008. "4D-CT motion estimation using deformable image registration and 5D respiratory motion modeling." Med. Phys. Vole 35 (10). 4577-4590.

Yorke, Ellen et al. 2005. "Interfractional anatomic variation in patients treated with respiration-gated radiotherapy." Journal of applied clinical medical physics. vol. 6, No. 2. 19-32.

Yu, Cedric X. et al. 1998. "The effects of intra-fraction organ motion on the delivery of dynamic intensity modulation." Phys. Med. Biol. vol. 43. 91-104.

Zhang, Qinghui et al. 2007. "A patient-specific respiratory model of anatomical motion for radiation treatment planning." Medical Physics, vol. 34. 4772-4781.

Zhao, Tianyu et al. 2008. "Characterization of free breathing patterns with 5D lung motion model." Med. Phys. vol. 36 (11). 5183-5189.

* cited by examiner

DEFORMABLE LUNG MODEL APPARATUS

CROSS REFERENCE TO RELATED APPLICATIONS

This application claims priority to U.S. Ser. No. 62/626,883, filed Feb. 6, 2018, the entire contents of which are incorporated herein by reference.

STATEMENT REGARDING GOVERNMENT SUPPORT

This invention was made with government support under Grant Number CA169102 awarded by The National Institutes of Health. The government has certain rights in the invention.

BACKGROUND OF THE INVENTION

Field of Invention

The present invention is related to a physical, anthropomorphic lung model for correlating external and internal motion in radiation oncology systems.

Discussion of the Background

In radiation therapy (RT), respiration induced anatomical motion can limit the accuracy of dose delivery for cancers in the thorax and abdomen. Improving the accuracy and precision of the dose delivery to a moving anatomy requires the ability to accurately capture the position of the tumor and the organs at risk (OAR) throughout the respiratory cycle, and to estimate the effect of the motion on the delivered dose and OARs To date, the most common approach for addressing respiratory motion has been to assume that the breathing pattern is periodic as a function of time. However, it is well-known that under free breathing conditions, many patients have irregular breathing patterns such that a periodic function is an inadequate characterization of the respiratory motion. In light of this fact, researchers have resorted to more sophisticated models in the frame work of motion prediction and real time estimation of respiratory motion models based on local regression methods. A clinical example of implementations of such models is the Synchrony system (Accuray Inc., CA) which uses real-time fluoroscopic tracking to build and update the relationship between external skin markers and internal fiducials placed in/near the tumor. Irrespective of whether the markers are internal or external, there are two main assumptions underlying current surrogate-based tumor tracking (i) the motion of the surrogates is correlated with that of the tumor target, and (ii) the correlation between the surrogates and the tumor target is constant.

The empirical validation and regular quality assurance of these techniques is usually performed using programmable motion phantoms that attempt to mimic the anatomical changes during respiration as closely as possible. These phantoms can evaluate and test a given motion management technique before it is deployed for clinical use. These phantoms can be categorized as rigid and deformable phantoms. An example of a fully rigid (rigid interior-rigid exterior) phantom was described by Starkschall et al. (see below), who modified a commercially available rigid motion phantom (supplied by the vendor of the respiratory monitoring system [Respiratory Position Management (RPM): Varian Medical Systems, Palo Alto Calif.]) to evaluate a set of parameters useful for assessment of the quality of four-dimensional (4D) computed-tomography (CT). A slightly irregular shaped wheel was used that would permit change in the vertical displacement of the RPM placed on top of the phantom, which is a common indicator of the anterior-posterior motion of the chest during the respiration.

In deformable phantoms, the extent of deformability, can dictate the potential of these phantoms to resemble the human anatomy during the respiration. Internal deformability is assumed to replicate the internal target/anatomy motion and the external deformability attempts to reproduce the visible motion of the chest and abdomen during respiration (external surrogate). Some extent of internal deformability is included in the majority of existing phantoms while there are only a few that produce the external motion. For example, Serban et al. (see below) used a cylinder filled with water and a latex balloon stuffed with dampened sponges to make an externally rigid-internally deformable (i.e. rigid and deformable) phantom. The internal motion was created using a piston attached to a programmable motor. The same phantom was later modified to simulate respiratory-induced lung tumor motion and deformation while the delivered dose was measured at different positions in the lung and the tumor in real time. Chang et al. (see below) have a similar phantom, but it had a more complex approach for transferring the periodic motion to the deformable interior including a silicon membrane instead of the perforated lid. Nioutsikou et al. (see below) managed to deliver and measure the dose in a cylindrical tumor that was embedded inside a tissue-equivalent breathing externally rigid-internally deformable phantom. Kashani et al. (see below) designed a phantom by inserting foam infused with iodine inside the exterior of a rigid commercial thoracic phantom (RS-330, Radiology Support Devices, Long Beach, Calif.) and simulated the internal SI motion by compressing and decompressing the inserts of the phantom. Niu et al. (see below) proposed a method to build an internally deformable phantom and used gel dosimeters to experimentally validate deformable dose algorithms by measuring their 3D distribution during the periodic motions and compared the results with delivered dose to the static control.

Remmert et al (see below) used porcine heart-lung explant to build a lung phantom with periodic motion to evaluate a new 4D-MRI method. The position of the piston rod is used for sorting the images and monitoring the motion of the dynamic lung phantom (surrogate signal) since the exterior of the phantom is rigid.

Court et al. (see below) used an externally and internally deformable (Radiology support devices, Inc., Long Beach, Calif.) breathing phantom. Two independent motion actuators have been used, a pump that inflates and deflates the lung, and a motor that moves the tumor inside the lung-based on patient derived trajectories. However, no relation or correlation exists between the motions of the tumor or the lung. The tumors are shaped from flexible resin material with the intensity equivalent to the real tumors. The delivered dose and the CT number is compared for different treatment planning methods.

The following references describing the state of the art are herein incorporated by reference in their entirety:
1. S. Vedam, P. Keall, V. Kini, H. Mostafavi, H. Shukla and R. Mohan, Physics in medicine and biology 48 (1), 45 (2002).
2. T. Pan, T. Y. Lee, E. Rietzel and G. T. Chen, Medical physics 31 (2), 333-340 (2004).
3. X. Y. Cedric, D. A. Jaffray and J. W. Wong, Physics in medicine and biology 43 (1), 91 (1998).

4. P. Keall, V. Kini, S. Vedam and R. Mohan, Physics in medicine and biology 46 (1), 1 (2001).
5. T. Bortfeld, S. B. Jiang and E. Rietzel, presented at the Seminars in radiation oncology, 2004 (unpublished).
6. A. E. Lujan, E. W. Larsen, J. M. Balter and R. K. Ten Haken, Medical physics 26 (5), 715-720 (1999).
7. Y. Seppenwoolde, H. Shirato, K. Kitamura, S. Shimizu, M. Van Herk, J. V. Lebesque and K. Miyasaka, International Journal of Radiation Oncology*Biology*Physics 53 (4), 822-834(2002).
8. T. Neicu, H. Shirato, Y. Seppenwoolde and S. B. Jiang, Physics in medicine and biology 48 (5), 587 (2003).
9. S. Nehmeh, Y. Erdi, T. Pan, E. Yorke, G. Mageras, K. Rosenzweig, H. Schoder, H. Mostafavi, O. Squire and A. Pevsner, Medical physics 31 (6), 1333-1338 (2004).
10. L. A. Dawson, K. K. Brock, S. Kazanjian, D. Fitch, C. J. McGinn, T. S. Lawrence, R. K. Ten Haken and
11. J. Balter, International Journal of Radiation Oncology*Biology*Physics 51 (5), 1410-1421 (2001).
12. E. Ford, G. Mageras, E. Yorke, K. Rosenzweig, R. Wagman and C. Ling, International Journal of Radiation Oncology*Biology*Physics 52 (2), 522-531(2002).
13. E. Yorke, K. E. Rosenzweig, R. Wagman and G. S. Mageras, Journal of applied clinical medical physics 6 (2), 19-32 (2005).
14. K. Malinowski, T. J. McAvoy, R. George, S. Dietrich and W. D. D'Souza, International Journal of Radiation Oncology*Biology*Physics 82 (5), 1665-1673 (2012).
15. M. J. Murphy and S. Dieterich, Physics in medicine and biology 51 (22), 5903 (2006).
16. G. C. Sharp, S. B. Jiang, S. Shimizu and H. Shirato, Physics in medicine and biology 49 (3), 425 (2004).
17. Q. Zhang, A. Pevsner, A. Hertanto, Y. C. Hu, K. E. Rosenzweig, C. C. Ling and G. S. Mageras, Medical Physics 34 (12), 4772-4781 (2007).
18. T. Zhao, W. Lu, D. Yang, S. Mutic, C. E. Noel, P. J. Parikh, J. D. Bradley and D. A. Low, Medical physics 36 (11), 5183-5189 (2009).
19. R. Li, J. H. Lewis, X. Jia, T. Zhao, W. Liu, S. Wuenschel, J. Lamb, D. Yang, D. A. Low and S. B. Jiang, Physics in medicine and biology 56 (18), 6009 (2011).
20. D. Yang, W. Lu, D. A. Low, J. O. Deasy, A. J. Hope and I. El Naga, Medical physics 35 (10), 4577-4590 (2008).
21. J. Tang, S. Dieterich and K. R. Cleary, presented at the Medical Imaging 2004, 2004 (unpublished).
22. G. Starkschall, N. Desai, P. Balter, K. Prado, D. Luo, D. Cody and T. Pan, Journal of Applied Clinical Medical Physics 8 (3), 1-20 (2007).
23. M. Serban, E. Heath, G. Stroian, D. L. Collins and J. Seuntjens, Medical physics 35 (3), 1094-1102 (2008).
24. L. E. Court, J. Seco, X. Q. Lu, K. Ebe, C. Mayo, D. Ionascu, B. Winey, N. Giakoumakis, M. Aristophanous and R. Berbeco, Medical physics 37 (11), 5850-5857 (2010).
25. J. Chang, T. S. Suh and D. S. Lee, Journal of applied clinical medical physics 11 (1), 281-286 (2010).
26. A. Cherpak, M. Serban, J. Seuntjens and J. E. Cygler, Medical physics 38 (1), 179-187 (2011).
27. E. Nioutsikou, J. R. N. Symonds-Tayler, J. L. Bedford and S. Webb, Physics in medicine and biology 51 (14), 3359 (2006).
28. C. J. Niu, W. D. Foltz, M. Velec, J. L. Moseley, A. Al-Mayah and K. K. Brock, Medical physics 39 (2), 765-776 (2012).
29. R. Kashani, K. Lam, D. Litzenberg and J. Balter, Medical physics 34 (1), 199-201 (2007).
30. G. Remmert, J. Biederer, F. Lohberger, M. Fabel and G. Hartmann, Physics in medicine and biology 52 (18), N401 (2007).
31. Y. Cheung and A. Sawant, Medical physics 42 (5), 2585-2593 (2015).
32. K. Malinowski, K. Lechleiter, J. Hubenschmidt, D. Low and P. Parikh, Medical Physics 34 (6), 2611-2611 (2007).
33. Y. Suh, S. Dieterich, B. Cho and P. J. Keall, Physics in medicine and biology 53 (13), 3623 (2008).
34. Y. Seppenwoolde, R. I. Berbeco, S. Nishioka, H. Shirato and B. Heijmen, Medical physics 34 (7), 2774-2784 (2007).
35. M. J. Murphy, J. Balter, S. Balter, J. A. BenComo, I. J. Das, S. B. Jiang, C. M. Ma, G. H. Olivera, R. F. Rodebaugh and K. J. Ruchala, Medical physics 34 (10), 4041-4063 (2007).
36. G. F. Persson, D. E. Nygaard, C. Brink, J. W. Jahn, P. M. of Rosenschold, L. Specht and S. S. Korreman, Radiotherapy and Oncology 96 (1), 61-66 (2010).
37. G. F. Persson, D. E. Nygaard, P. M. of Rosenschold, I. R. Vogelius, M. Josipovic, L. Specht and S. S. Korreman, International Journal of Radiation Oncology*Biology*Physics 80 (5), 1573-1580 (2011).
38. J. Cai, P. W. Read, J. M. Baisden, J. M. Larner, S. H. Benedict and K. Sheng, International Journal of Radiation Oncology*Biology*Physics 69 (3), 895-902 (2007).
39. J. Sarker, A. Chu, K. Mui, J. A. Wolfgang, A. E. Hirsch, G. T. Chen and G. C. Sharp, Medical physics 37 (3), 1254-1260 (2010).
40. S. S. James, P. Mishra, F. Hacker, R. I. Berbeco and J. H. Lewis, Physics in medicine and biology 57 (5), L1 (2012).

SUMMARY OF THE INVENTION

According to one embodiment, there is provided a lung motion phantom device comprising a body having an outer shell and a lung insert, a first actuator connected to a first drive linkage for a first displacement of an internal volume of the lung insert and an outer surface of the outer shell in a first direction, a second actuator connected to a second drive linkage for a second displacement of the internal volume of the lung insert and the outer surface of the outer shell in a second direction different than the first direction, and a controller programmed to independently control the first and second actuators such that the first and second displacements simulate movement of an external surface and an interior of a thoracic region of a patient.

According to one embodiment, there is provided a method of predicting where a target site inside a patient moves in time. This method utilizes a deformable phantom having a size and a shape characteristic of a patient. With at least two actuators, programmed with mathematical or patient recorded motion trajectories, deform the phantom in at least two directions to simulate motion of the target site inside the patient. The temporal position of a marker attached to or inside the phantom is tracked.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
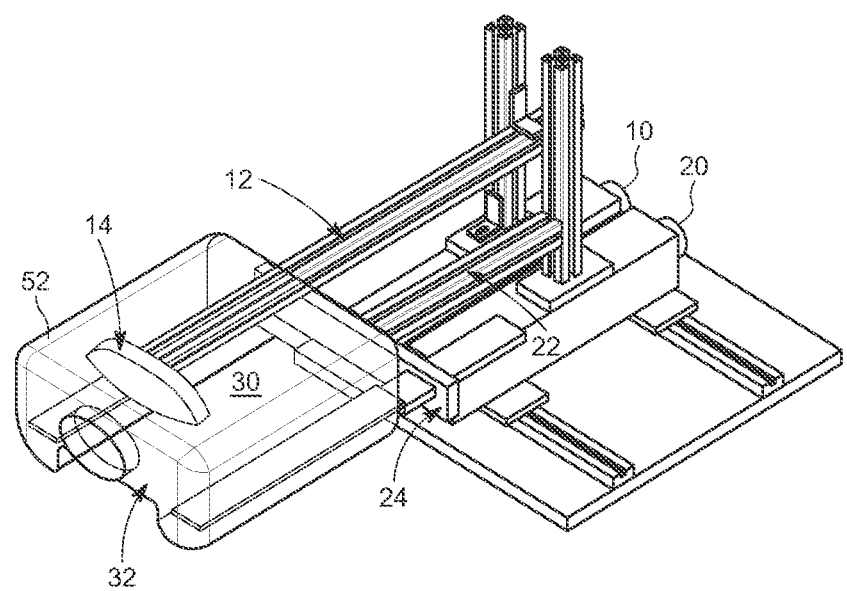
FIG. 1A is an illustrative schematic of an anthropomorphic lung motion phantom device, according to one embodiment of the present invention, showing maximum superior-inferior (SI) displacement.

With the exception of the phantom described by Court et al. (see above), all of the aforementioned phantom designs were based on a rigid exterior. Such designs do not adequately represent respiration because during the respiration the tumor and the surrounding critical organs move relative to each other in human body. The present inventors in reference #30 noted above previously presented an externally-internally deformable phantom that used a high-precision motion platform (MP), programmed with patient-derived motion trajectories, to actuate motion by compressing and decompressing a deformable insert. In this phantom, the correlated internal and external motion of the human anatomy was replicated. However, the present inventors discovered that the correlated motion of these devices failed to accurately represent the varying amounts of engagement of thoracic and abdominal muscles from respiratory cycle to cycle. This limitation was also discovered by the present inventors to be present in typical phantom designs, such as those that used a single motion actuator. Therefore, at the time of the present invention, there was a need for a tool to incorporate variability of correlation between internal lung motion and external surface motion.

Referring to FIGS. 1A, 1B, 2A, 2B, 3A, 3B, 3C, and 8, provided herein is a schematic drawing of an anthropomorphic lung motion phantom device, according to various embodiments of the invention. The phantom device in one embodiment is configured to closely simulate respiratory motion and patient-derived motion trajectories. In one embodiment, the phantom device is externally and internally deformable, and in another embodiment is programmable with mathematical (e.g., sinusoidal) functions or physiological motion trajectories recorded from tumors/organs of patients. The phantom device includes multiple independently programmable linear actuators to compress and decompress a variable-stiffness insert. By programming these actuators with distinctly different motion trajectories (example differences include phase, amplitude, frequency), the phantom device can be configured to produce variably correlated motion between different portions of the phantom. An example of variable correlation is when an external marker moves ±5 mm, an internal marker moves ±2 mm in the first five seconds, ±5 mm in the next five seconds, ±1 mm in the following five seconds, and so on. Such variable correlation can occur between any two or more points or sub-regions within the internal volume of the phantom, or any two or more points or sub-regions on the external surface of the phantom, or between any one or more points or sub-regions within the internal volume of the phantom and one or more points or sub-regions on the external surface of the phantom. In one embodiment, independently programmable actuators allow a user (e.g., by user input) to change the external-to-internal correlation of the internal volume and the external surface in a generally reproducible manner, and also independently change the amplitude of motion, such as superior-inferior (SI) and anterior-posterior (AP) motions. The phantom device, therefore, can simulate human thoracic anatomy undergoing respiration for treatment planning of radiation oncology procedures.

Figure 1B:
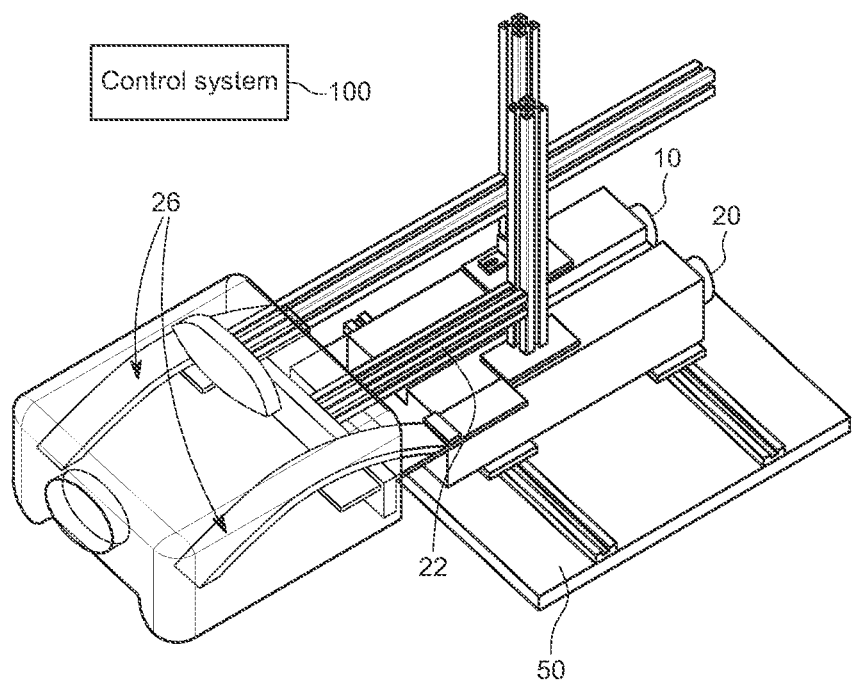
FIG. 1B is an illustrative schematic of the anthropomorphic lung motion phantom device of FIG. 1B, showing maximum anterior-posterior (AP) displacement.

FIG. 1A is a schematic of an anthropomorphic lung motion phantom device, according to one embodiment of the present invention. More specifically, FIG. 1A shows an actuator 10 connected to linkage 12 (the SI arm) which connects to the SI push plate 14 which, as shown in FIG. 1A, is at the maximum superior-inferior (SI) displacement. The SI push plate 14 pushes against a lung insert 34 (not shown here) inside the body of phantom 30 to displace the lung insert in a SI direction (a first direction). FIG. 1B is an illustration of a schematic of the anthropomorphic lung motion phantom device of FIG. 1B. More specifically, FIG. 1B shows an actuator 20 connected to linkage 22 (the AP arm) which connects to the AP push plate 24 which, as shown in FIG. 1B is at maximum anterior-posterior (AP) displacement. The AP push plate 24 pushes against an end of at least one binding strip 26 (flexible strips) which deflect upward in the AP direction (a second direction). In FIG. 1A, there is no flexion in the AP flexible strips 26 as the AP push plate 24 is at its most inferior position. In FIG. 1B, the AP push plate 24 has maximum displacement causing the maximum bend in the flexible strips 26.

Figure 2A:
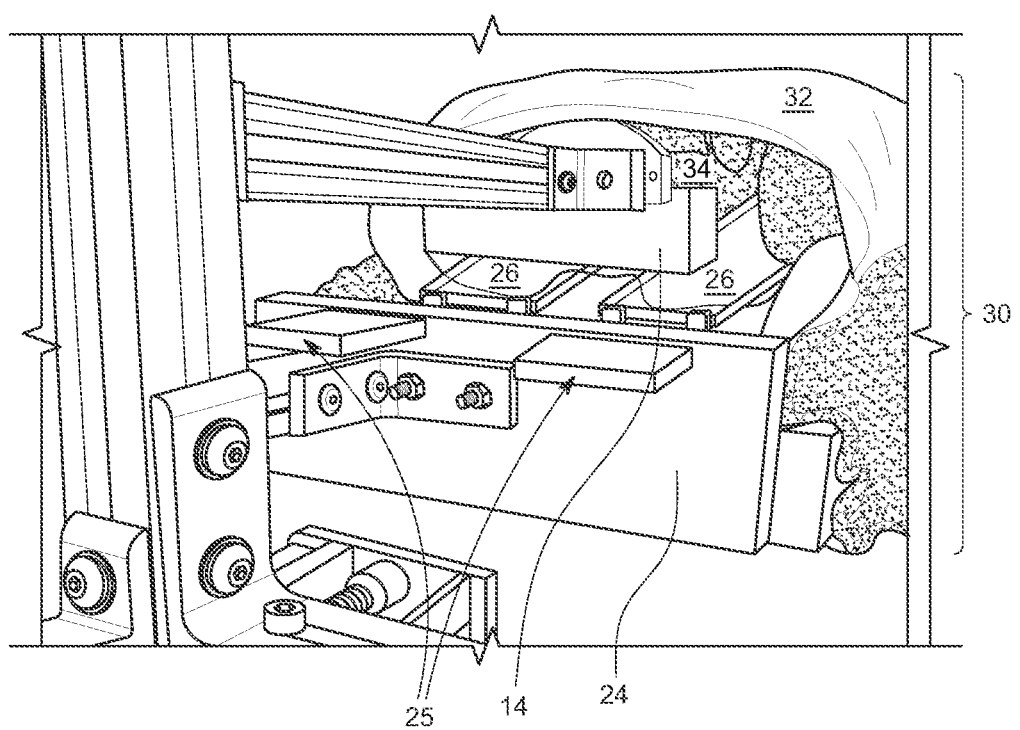
FIG. 2A is a depiction of a posterior view of the shell of anthropomorphic lung motion phantom device of FIGS. 1A and 1B.
Figure 2B:
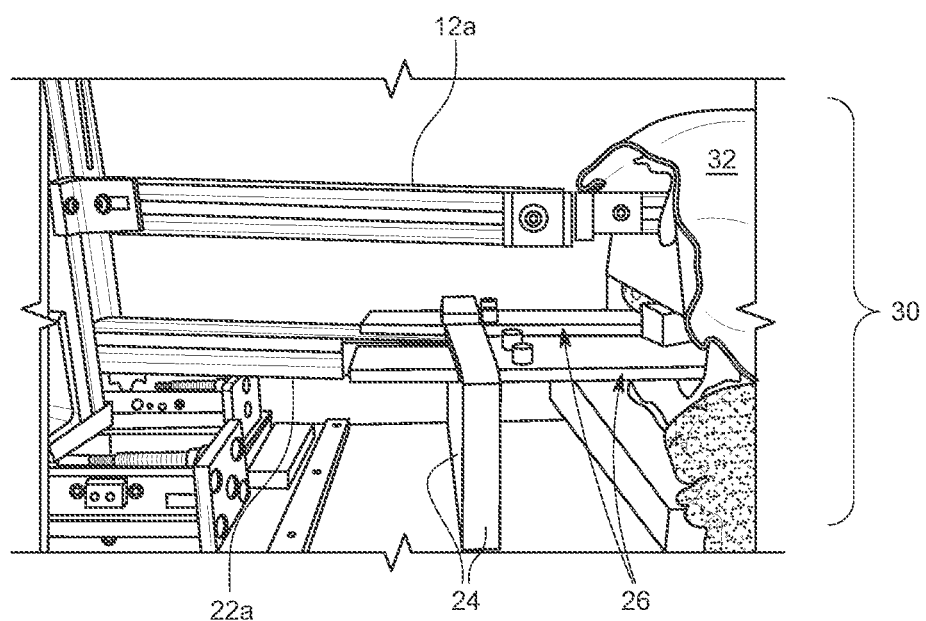
FIG. 2B is a depiction of a lateral view of rigid rods of the anthropomorphic lung motion phantom device of FIGS. 1A and 1B.

FIG. 2A is a back view depiction of the shell 32 of the anthropomorphic lung motion phantom device of FIGS. 1A and 1B. FIG. 2A shows a close-up view of the SI push plate 14 pushing against an end of lung insert 34. This push expands the flexible lung insert. The SI push plate 14 is configured to be adjustable to different angles. with adjustable angle. FIG. 2A also shows the AP push plate 24 attached to rigid rods 25 which engage the bending strips 26 disposed under lung insert 34. As the bending strips bend upward, the lung insert is raised upward in the SI direction. FIG. 2B is a depiction of a lateral view of the anthropomorphic lung motion phantom device of FIGS. 1A and 1B. FIG. 2B shows details of linkage 12 (the SI arm) and linkage 22 (the AP arm).

One embodiment, again referring to FIGS. 1A, 1B, 2A, 2B, 3A, 3B, 3C, and 8, includes an outer shell 32, a SI mechanism (such as linkage 12), an AP mechanism (such as linkage 22), and a control system 100. The phantom 30 has an outer shell 32 which includes an outer surface 34 that is movable to simulate up and down motion (e.g., AP) of a patient's chest surface in response to respiration, as further described below, and a lung insert 34. The outer shell 32, for example, may be a commercially-available lung module (RS-1500, Radiology Support Devices, Inc., Long Beach, Calif.) having a rigid posterior half and a flexible anterior half. The lung insert 34 fills a volume formed by the outer shell, and in at least one embodiment the lung insert is made from a natural latex foam.

The AP mechanism is configured to deform the lung insert 34 and the outer shell 32, and thus the outer surface, in a generally AP motion. In the one embodiment, the AP mechanism includes a set of flexible strips 26, an AP push plate 24, and an AP actuator 20. In one embodiment, the flexible strips 26 have a first end fixed to a posterior portion of the outer shell 34 and a second end fixed to the AP plate 24. Each of the first end and the second end may be fixable at various points of the posterior portion and the AP plate, respectively, such that the flexible strips have an adjustable stiffness, as further described below. In the one embodiment, the second end is fixable at various points of the posterior portion by fixing to (or pressing against) one of a series of indexed slats, thus adjusting an effective length and stiffness of the flexible strips. Other types of fixation may be used to adjust the effective length, such as by using sliding bolt-and-slot and the like. In one embodiment, the AP mechanism 22 is generally positioned in a bottom portion of the outer shell, which generally correlates to an area near the spinal cord of a patient.

The flexible strips 26 are generally oriented along the superior-inferior (i.e. cranio-caudal) direction of the phantom device, although flexible strips of some embodiments may be aligned in other orientations, such as diagonally relative to the superior-inferior and/or anterior-posterior directions. In one embodiment, the flexible strips 26 are made of multiple layers of flexible composites, such as three layers of Plexiglas®, or the like. For example, multiple layers may be preferable to allow the flexible strips to bend in a predictable and preferred manner. Furthermore, in the one embodiment the AP push plate 24 is coupled to the AP actuator 20 via a rigid rod such as AP linkage 22, while in some embodiments the AP push plate 24 is directly coupled to the AP actuator 20 without a rigid rod.

As discussed above, the set of flexible strips 26 can be fixed to a posterior portion of outer shell 32 of phantom 30. The set of flexible strips 26 can be fixed using many common methods, including adhesives, cements, epoxies, friction-fit, and/or fasteners. In the one embodiment, the set of flexible strips are fixed to the poster portion of the outer shell by a cement, such as Weld-On® Multi-Purpose Cement, and are coupled to the AP push plate 24 at the second end. For example, the AP push plate 24 may be a plate formed of a plastic, such as Nylon, metal, composite, or the like. As a further example, the AP push plate 24 may be a Nylon plate having a thickness of 2 cm.

Each of the AP actuator 20 and the SI actuator 10 are independently programmable linear motion actuators. As further discussed below, the SI actuator 10 is coupled via the SI push plate 14 to the lung insert 34 to generate primarily SI motion, and the AP actuator 20 is coupled to the set of flexible strips 26 via the AP push plate 24 to generate primarily AP motion. The translational motion of the AP push plate 24 via displacement of the AP actuator 20 causes the set of flexible strips 26 to bend. For example, the AP push plate 24 places generally longitudinal forces on the set of flexible strips 26 between the first end and the second end such that the flexible strips buckle in accordance with the stiffness of the flexible strips and applied forces of the AP actuator and SI actuator (e.g., by the displacement of the AP actuator). The flexible strips 26 bend (i.e. buckle) between the first end and the second end to place a force on the lung insert 34 in a generally AP direction (e.g., upward). The flexible strips 26 may have maximum point of force between the first end and the second end that is adjustable, and generally depends on the stiffness of the set of flexible strips and the rigid rods.

The SI mechanism is configured to cause displacement of outer surface of the phantom 30 generally in the SI (e.g., cranio-caudal) direction. As discussed above, motion in the SI direction is generally caused by the SI actuator 10 of the SI mechanism pushing the lung insert 34 via the SI plate 14 in the SI (e.g., cranio-caudal) direction. In one embodiment, the SI plate 14 is generally positioned in a top portion of the outer shell. Furthermore, the connecting arm may have various length and/or slope. Thus, the SI mechanism and the SI push plate are configured to be adjustable.

In the one embodiment, referring to FIGS. 1A, 1B, 2A, and 2B, the rigid rods of the AP mechanism and the SI mechanism are formed of T-slots. (12a, 22a). Each of the T-slots (12a, 22a) and the AP push plate 24 and the SI push plate 14, respectively, form a link between the outer shell and the respective actuators. The lung insert 34 is positioned within the outer shell 32 and independently compressed by the AP push plate 24 and the SI push plate 14, as described above.

In another embodiment, the lung insert 34 is embedded with radio-opaque fiducial markers 38 configured to be measured while the phantom 30 is in operation. For example, the outer shell 32 and lung insert 34 may include, as radio-opaque fiducial markers, glass marbles. In one embodiment of the invention, data from the radio-opaque fiducial markers is used in tumor models to track the internal motion at different locations within the outer shell and on the outer surface (see FIGS. 3A, 3B, and 8). For example, the tumor models may be custom-formed by importing the contours of a tumor from a patient's computed tomography scan (standard-of-care for thoracic and abdominal cancer patients) into an additive manufacturing system such as a three-dimensional 3D printer.

In one embodiment, the AP mechanism 12, the SI mechanism 22, and the outer shell 32 of phantom 30 are in fixed positions to provide generally reproducible motion. In the one embodiment, the SI mechanism 22, and the outer shell 32 are fixed to a base plate 50, and the outer shell 32 is fixed to a box 52 containing the phantom 30, that are each securable to a typical CT-couch, for example, using lock bars or the like. Furthermore, the base plate 50 can be configured such that the position of each of the AP actuator 10 and the SI actuator 20 are adjustable, (e.g., along x- and y-axes of the base plate and/or the CT-couch).

In this invention, the first and second directions described above for phantom displacement need not adhere strictly to SI and AP directions. Movement in arbitrarily different directions may still produce replication of human lung movement or more generally the movement of an organ in the body subject to natural or patient-derived motion. Indeed, while the invention here is described with respect to lung motion, the present phantom can be used to replicate and track the trajectories of target sites such as tumors inside a patient as those sites would be expected to move due to natural, involuntary movements as well as patient derived motions.

Motion Trajectory Data

Furthermore, each of the AP actuator 20 and the SI actuator 10 are configured to allow independent motion from the other. Thus, each of the AP actuator 20 and the SI actuator 10 can receive independent input trajectories from control system 100. For example, each of the AP actuator 20 and the SI actuator 10 can be programmed to have in-sync motion, out-of-sync motion, and/or motion with a variable correlation. In one embodiment, patient-derived tumor traces (FIGS. 4A-4D) are obtained from a database such as the one created by Suh et al. (referenced above) using the CyberKnife Synchrony motion system that provides the tumor respiratory motion in three SI, AP, and left-right directions.

Figure 3A:
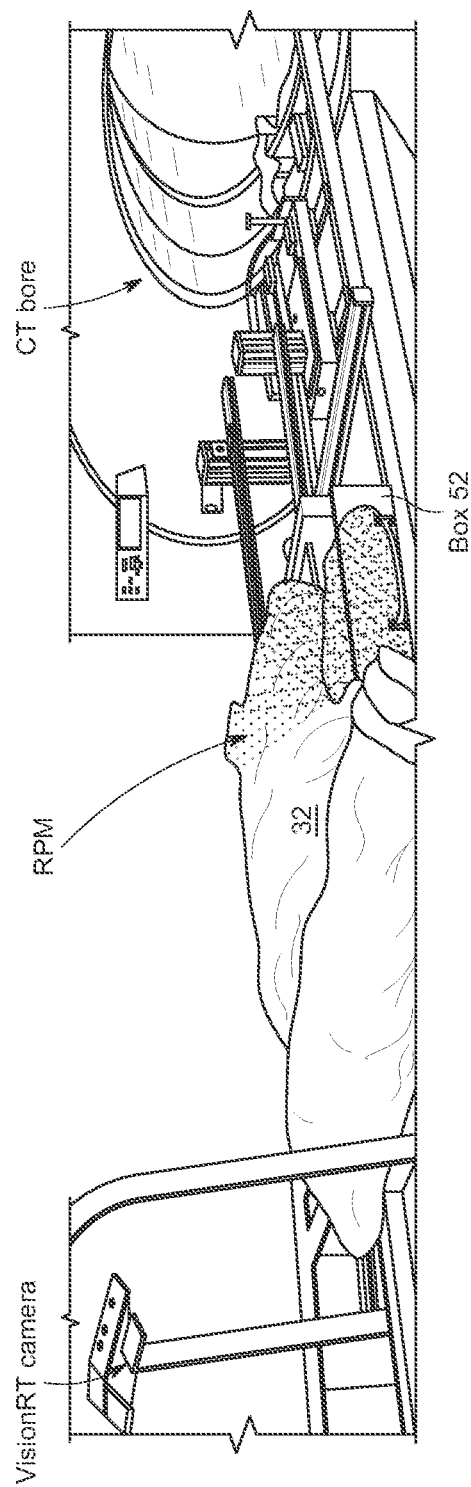
FIG. 3A is a depiction of an experimental setup of the anthropomorphic lung motion phantom device of FIGS. 1A and 1B, shown in a simulated computed tomography machine.

In one example of using the phantom device, each of the AP actuator and the SI actuator was programmed with in-sync and out-of-sync sinusoidal waves to characterize the resulting external AP motion and internal SI motion. FIG. 3A is a depiction of an experimental setup of the anthropomorphic lung motion phantom device of FIGS. 1A and 1B, shown in a simulated computed tomography machine, where results from the radio-opaque markers are used by the control system 100 to predict actual trajectories of a tumor or target site under a CT scan. This data can then be used with the imaging software of the CT system to obtain better CT resolution of the tumor.

Figure 3B:
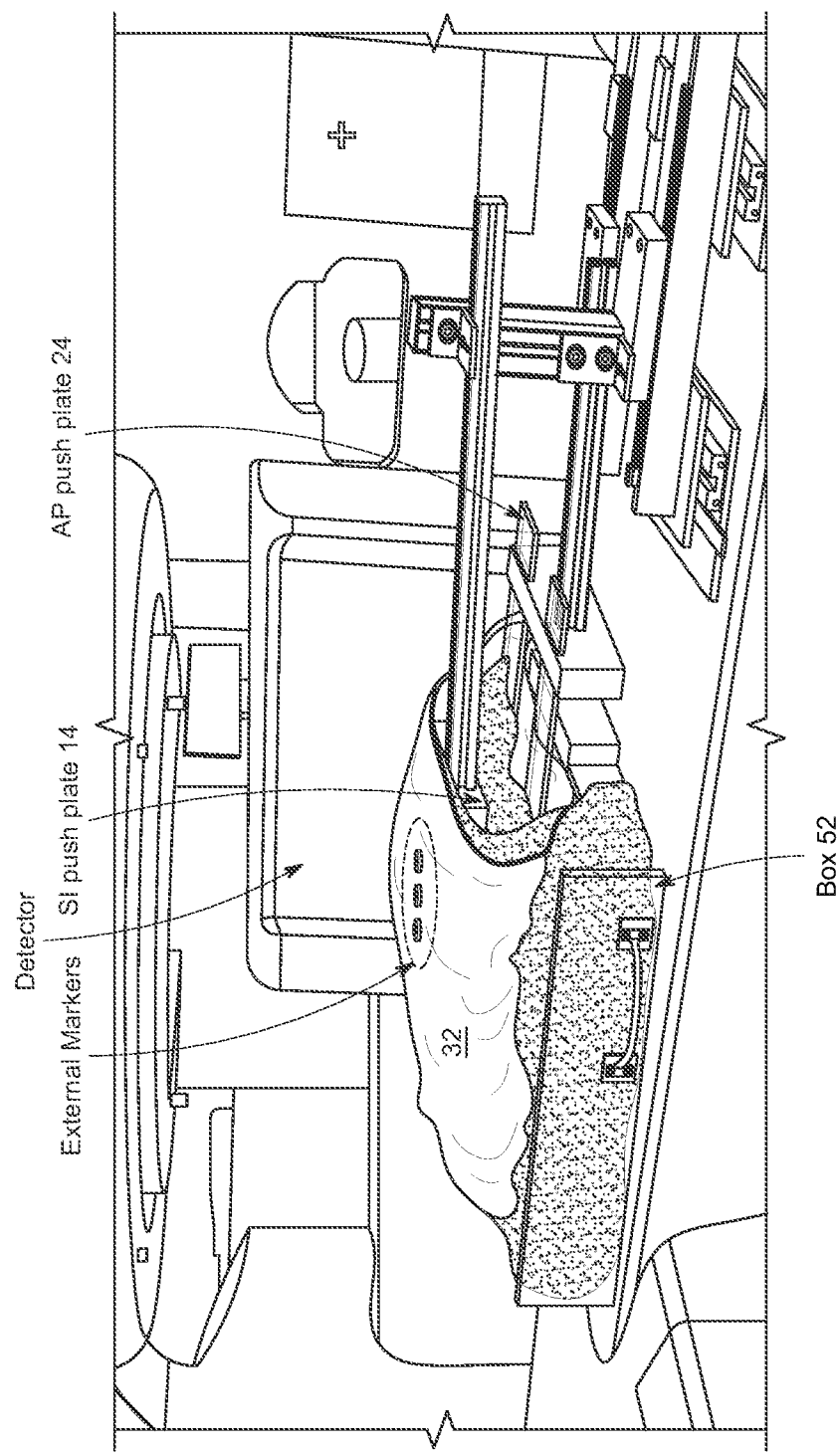
FIG. 3B is a depiction of an experimental setup of the anthropomorphic lung motion phantom device of FIGS. 1A and 1B, shown in a linear accelerator (LINAC) room.
Figure 3C:
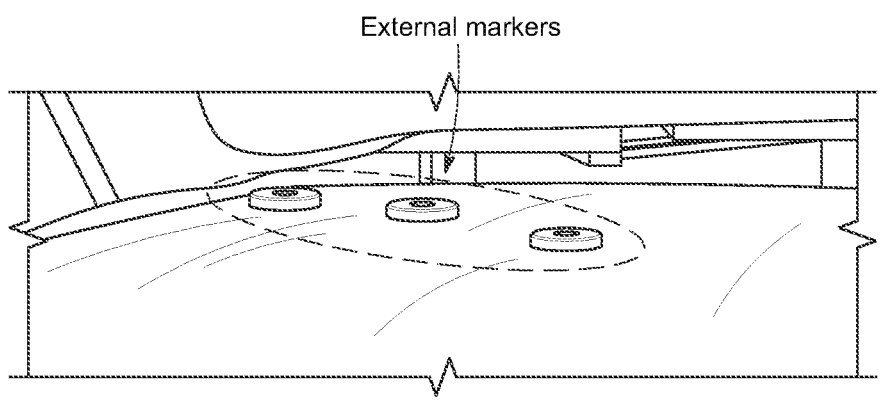
FIG. 3C is a close up depiction of the external markers on the experimental setup of the anthropomorphic lung motion phantom.
Figure 4A:
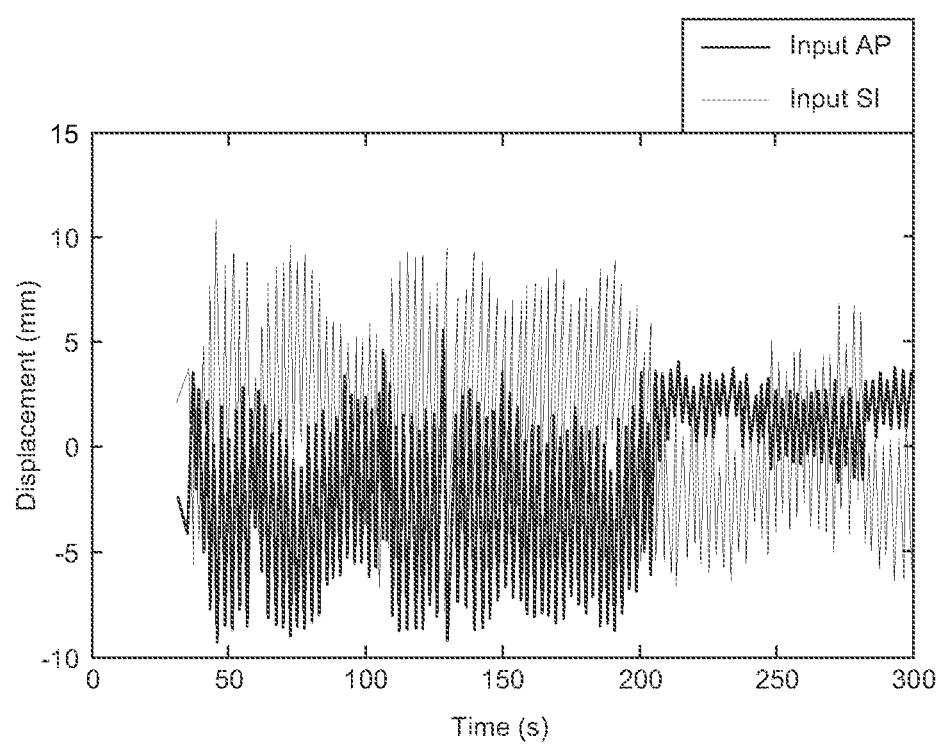
FIGS. 4A-4D are patient tumor traces used as input trajectories with the anthropomorphic lung motion phantom device of FIGS. 1A and 1B.
Figure 4B:
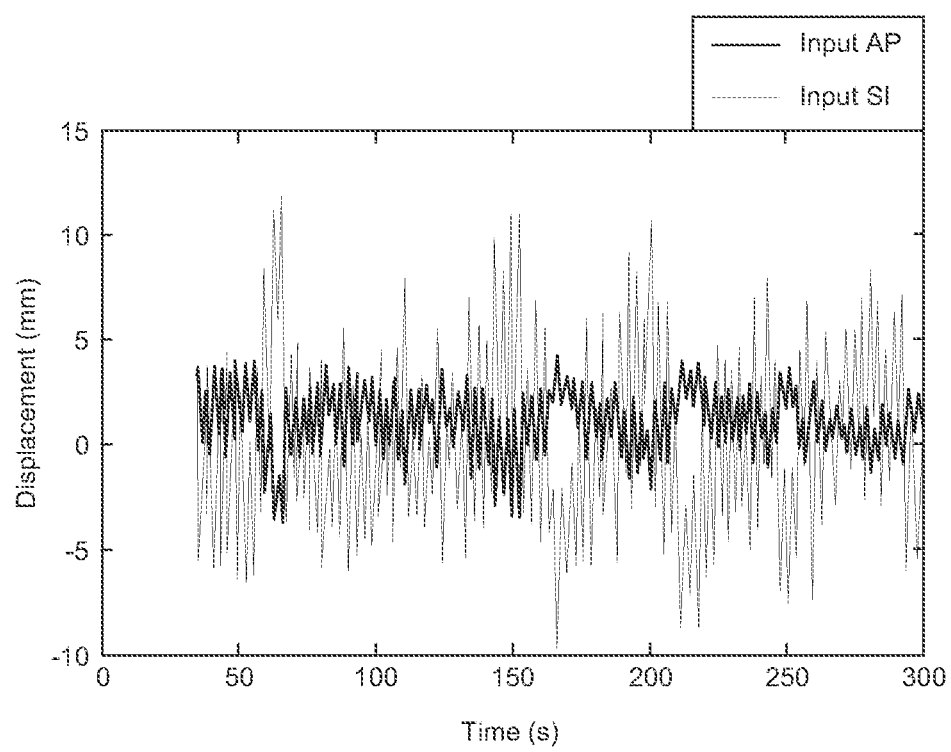
Figure 4C:
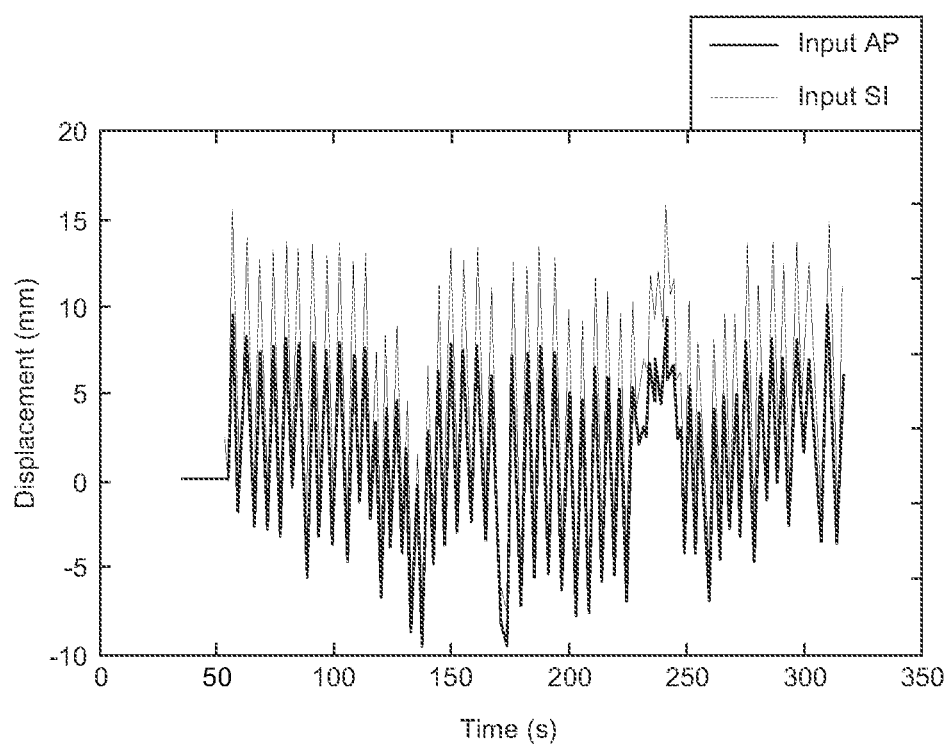
Figure 4D:
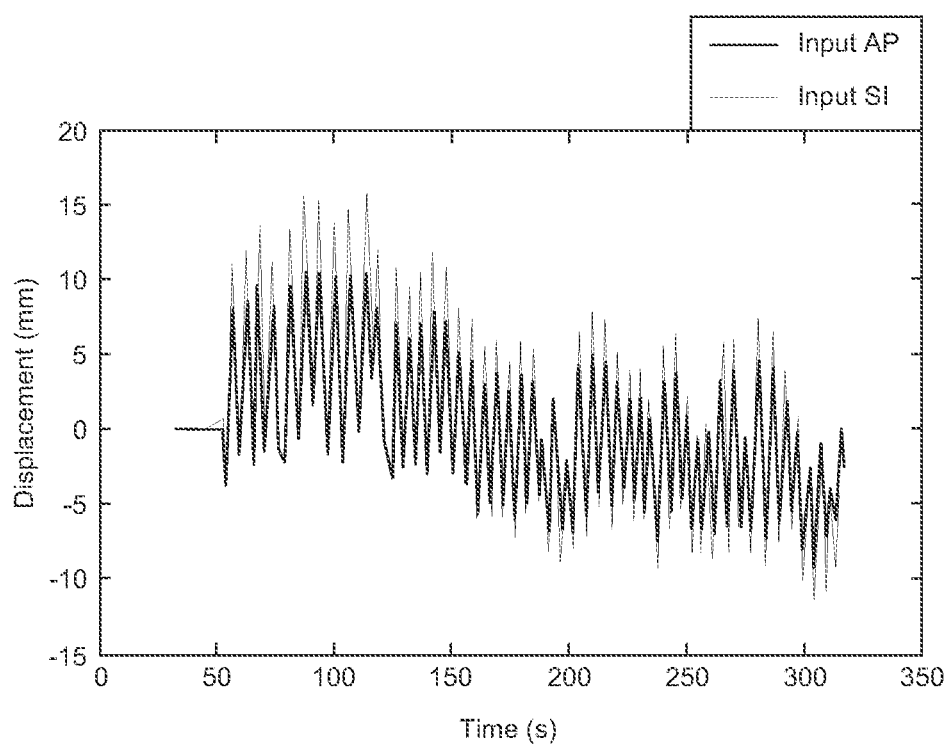

Similarly, FIG. 3B is a depiction of an experimental setup of the anthropomorphic lung motion phantom device of FIGS. 1A and 1B, shown in a linear accelerator (LINAC) room, where results from the radio-opaque markers are used by the control system 100 to predict actual trajectories of a tumor or target site exposed to the LINAC radiation. FIG. 3C is a close up depiction of the external markers on the experimental setup of the anthropomorphic lung motion phantom according to one embodiment.

FIGS. 4A-4D are patient tumor traces used as input trajectories with the anthropomorphic lung motion phantom device of FIGS. 1A and 1B. For example, the SI motion trace and AP motion trace from the Suh study were programmed on the x and z axes of the phantom device, respectively to generate the corresponding motion. Thus, the effect of change in the correlation of AP and SI motion of the tumor on AP displacement of external marker versus SI displacement of internal marker was observable (see FIGS. 5A, 5B, 6A, 6B, 7A, and 7B).

Validation of Variation in the Correlation of Internal and External Motion:

In another example, inputting sinusoidal waves of different amplitudes and zero phase shifts on the x (SI) and z (AP) axes of the phantom device (i.e. in-sync sinusoidal as input for SI and AP actuators) verified the ability of phantom device for creating constant correlated motions between the outer surface and internal surrogates (such as fiducials, the tumor model, or the like) and/or markers. Each of the AP motion and the SI trajectory of all the external and internal markers were extracted from fluoroscopic data (see FIG. 8).

Figure 5A:
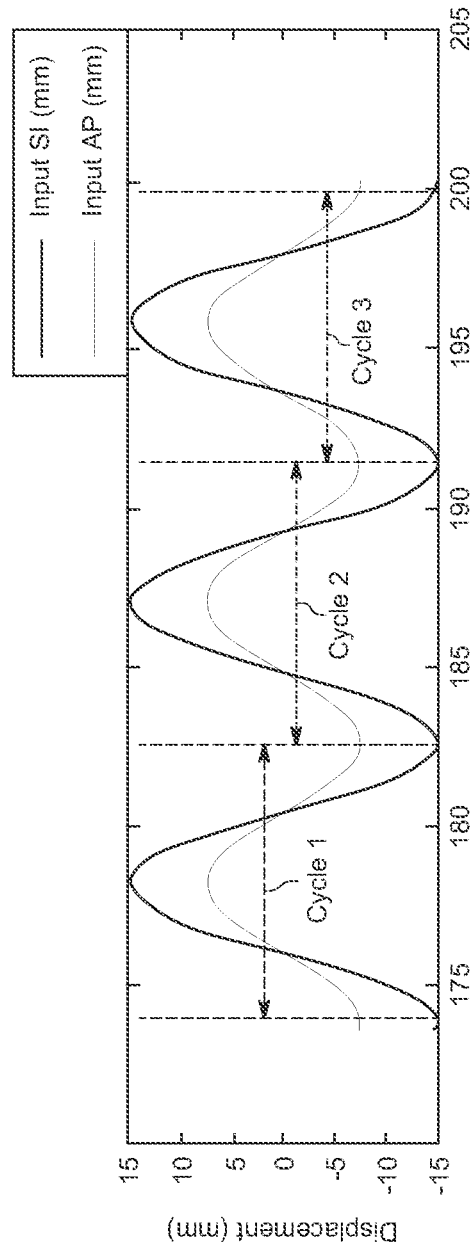
FIG. 5A is a graph showing three cycles of input in-sync sinusoidal trajectory for SI and AP actuators of the anthropomorphic lung motion phantom device of FIGS. 1A and 1B.
Figure 5B:
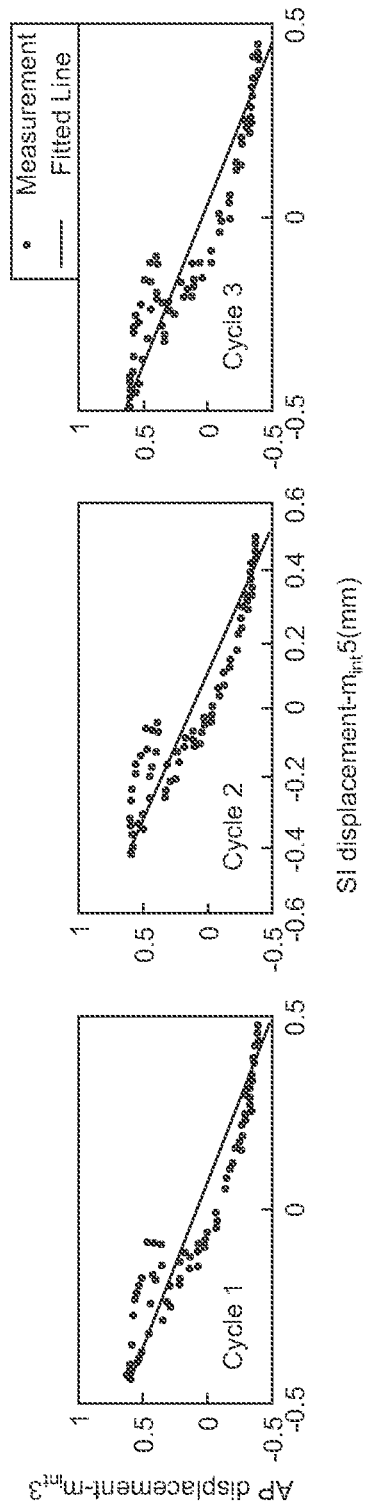
FIG. 5B is a set of graphs showing the correlation of AP displacement of third external marker ($m_{ext}3$) and SI displacement of fifth internal marker ($m_{int}5$), of the anthropomorphic lung motion phantom device of FIGS. 1A and 1B, for three exemplary cycles and a fitted line to the measured data points.

For example, the data for external marker 3 ($m_{ext}3$) and internal marker 5 ($m_{int}5$) are shown in FIGS. 5A and 5B. FIG. 5A is a graph showing three cycles of input in-sync sinusoidal trajectory for SI and AP actuators of the anthropomorphic lung motion phantom device of FIGS. 1A and 1B. FIG. 5B is a set of graphs showing the correlation of AP displacement of third external marker ($m_{ext}3$) and SI displacement of fifth internal marker ($m_{int}5$), of the anthropomorphic lung motion phantom device of FIGS. 1A and 1B, for three exemplary cycles and a fitted line to the measured data points The AP displacement of the $m_{ext}3$ generally correlates with the SI displacement of the $m_{int}5$ for three cycles, as shown in FIGS. 5A and 5B, when the AP and SI trajectories are in-sync, meaning that the two have a constant correlation. Furthermore, the general correlation is linear and without intra-cycle (i.e. variation of motion within a single breathing cycle) or inter-cycle variations (i.e. variation of motion between breathing cycles). Thus, a line can be fitted to the data and the slope and length of the line remains constant for all of the cycles (FIG. 5B).

Figure 6A:
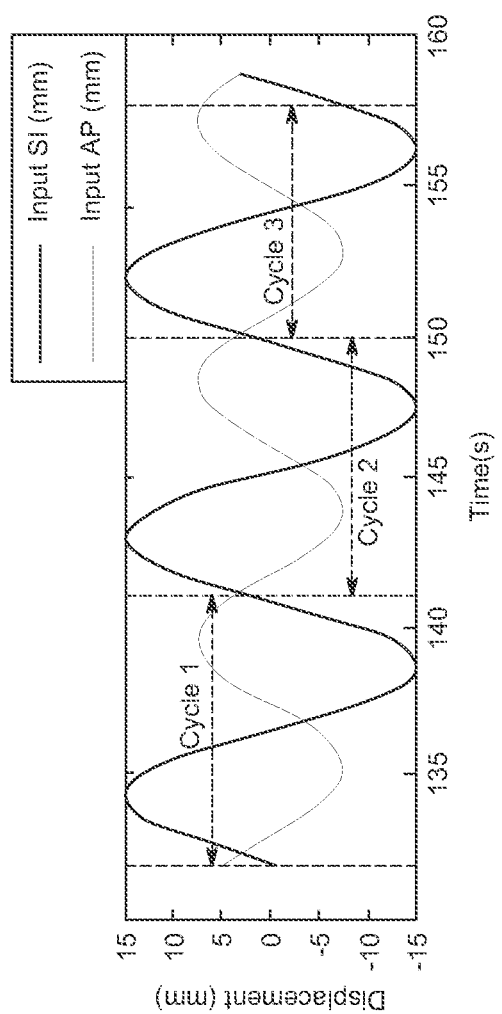
FIG. 6A is a graph showing three cycles of input out-of-sync sinusoidal trajectory for SI and AP actuators of the anthropomorphic lung motion phantom device of FIGS. 1A and 1B.
Figure 6B:
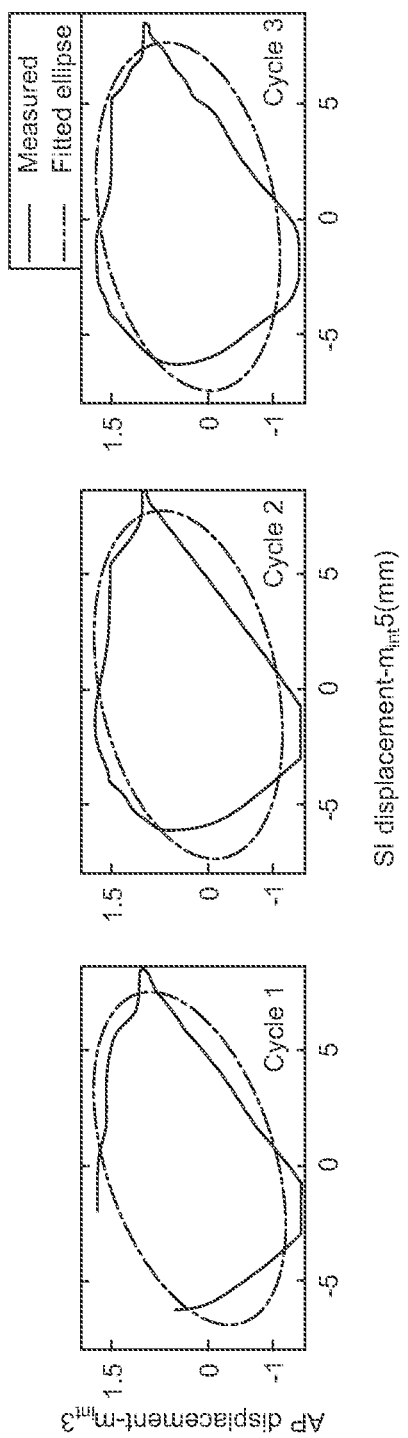
FIG. 6B is a set of graphs showing the correlation of AP displacement of external marker ($m_{ext}3$) and SI displacement of internal marker ($m_{int}5$), of the anthropomorphic lung motion phantom device of FIGS. 1A and 1B, for three cycles and a fitted line to the data points.

In another example, out-of-sync sinusoidal input trajectories on the two axes were measured (see FIGS. 6A and 6B). FIG. 6A is a graph showing three cycles of input out-of-sync sinusoidal trajectory for SI and AP actuators of the anthropomorphic lung motion phantom device of FIGS. 1A and 1B. FIG. 6B is a set of graphs showing the correlation of AP displacement of external marker ($m_{ext}3$) and SI displacement of internal marker ($m_{int}5$), of the anthropomorphic lung motion phantom device of FIGS. 1A and 1B, for three cycles and a fitted line to the data points.

The corresponding trajectory and correlation of the AP displacement of the $m_{ext}3$ and the SI displacement of $m_{int}5$ can be seen in FIGS. 6A and 6B. A line would not be an adequate representative of the correlation data points as the data has hysteresis, thus an ellipse is fitted. As shown in FIGS. 6A and 6B, the SI displacement of the $m_{int}5$ and AP displacement of the $m_{ext}3$ generally have hysteresis variation. The centroid of the fitted ellipse is located in the same location in all the cycles and the same lengths of the major and minor axes are seen for all of the cycles. In addition, there is no change in the rotation angle of the major axis of the fitted ellipse between the cycles. Unchanged rotation of the major axis can be interpreted as the constant correlation of AP displacement of external marker and SI displacement of internal marker between the cycles (see FIGS. 6A and 6B).

FIG. 5B represents an example of constant correlation. FIG. 6B represents an example of (cycle-to-cycle) variable correlation. Constant correlation is achieved when both motion actuators are programmed with identical and/or in-phase trajectories. Variable correlation (described below) is achieved when the two actuators are programmed with out-of-phase motion trajectories. For example, patient-derived trajectories in the AP and SI directions, when programmed into the two motion actuators will invariably give variable correlation.

Figure 7A:
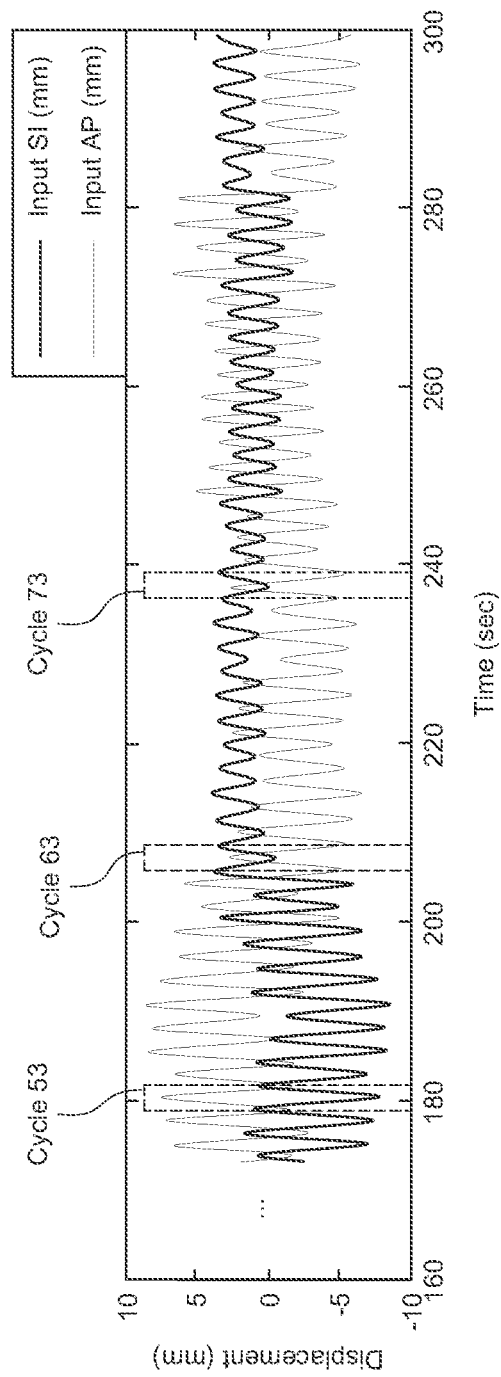
FIG. 7A is an example of patient-derived tumor trances, showing an input trajectory for SI and AP actuators of MP.
Figure 7B:
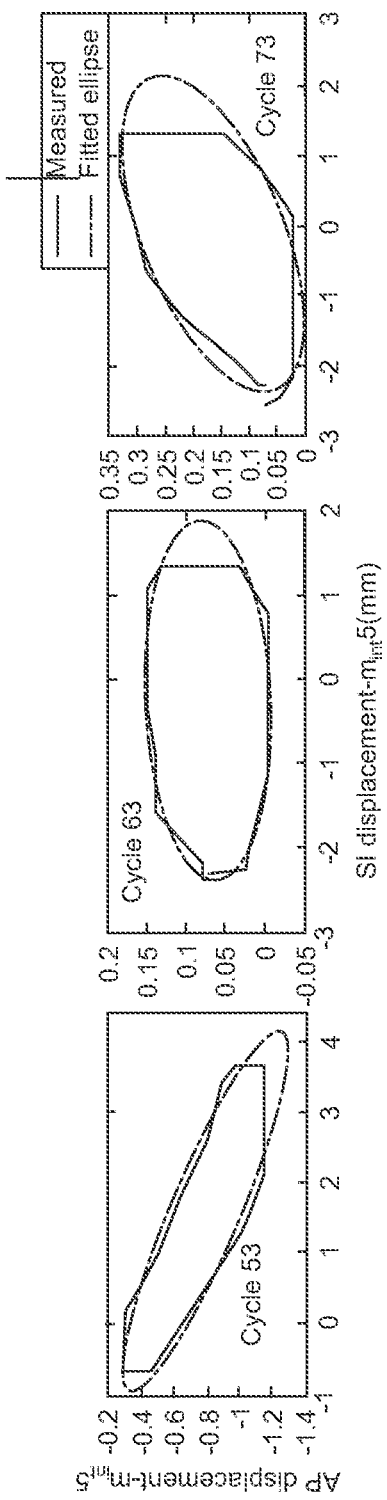
FIG. 7B is a set of graphs showing the correlation of AP displacement of external marker ($m_{ext}3$) and SI displacement of internal marker ($m_{int}5$) for the three exemplary cycles and fitted ellipse.
Figure 8:
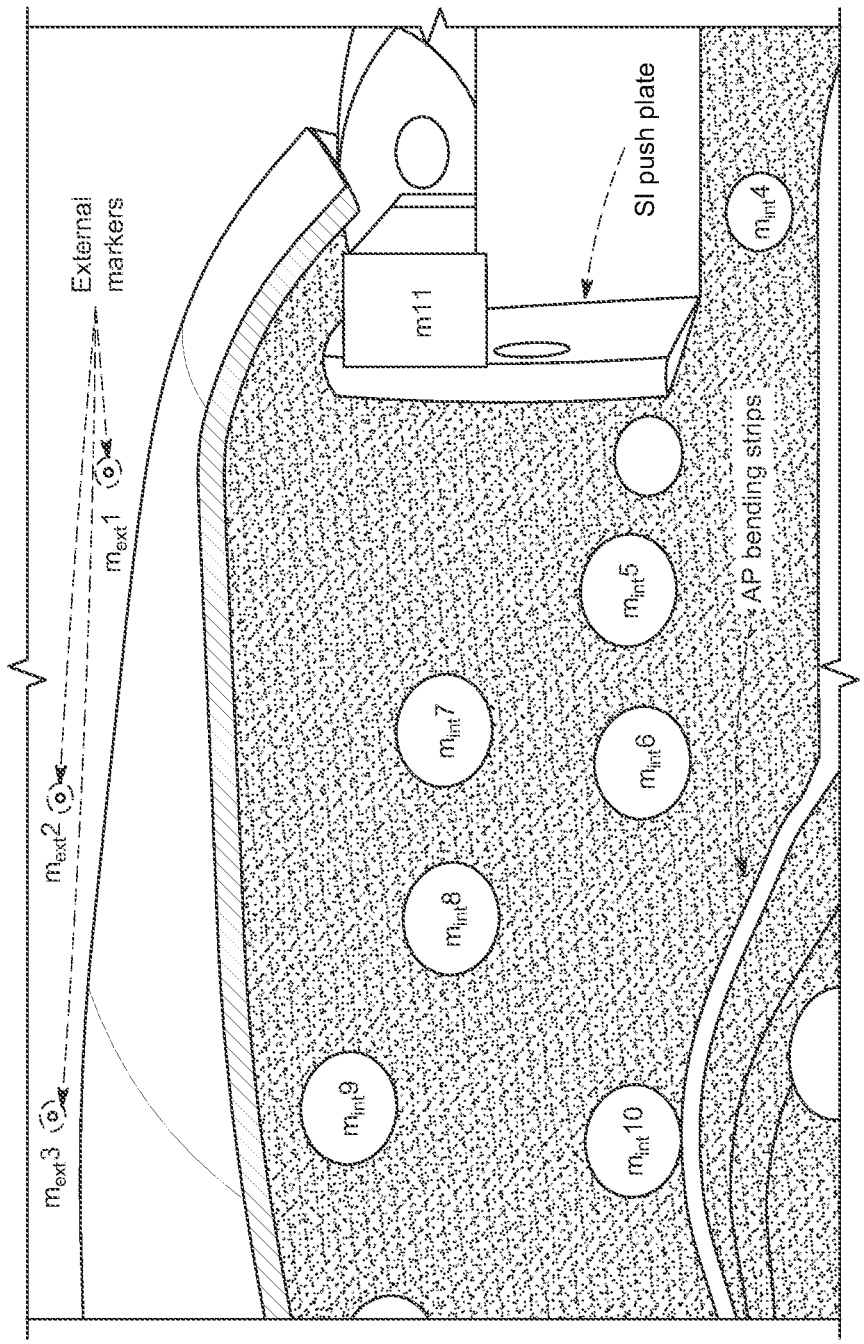
FIG. 8 is a sagittal fluoroscopic image of the anthropomorphic lung motion phantom device of FIGS. 1A and 1B.

Patient tumor traces for AP and SI motion trajectories were programmed on the AP and SI axes of the phantom device. Correlation of the AP displacement of the $m_{ext}3$ and SI displacement of $m_{int}5$ for three cycles of patient breathing are plotted in FIGS. 7A and 7B. FIG. 7A is an example of patient-derived tumor trances, showing an input trajectory for SI and AP actuators of MP. FIG. 7B is a set of graphs showing the correlation of AP displacement of external marker ($m_{ext}3$) and SI displacement of internal marker ($m_{int}5$) for the three exemplary cycles and fitted ellipse.

In the example of patient tumor traces, both inter-cycle and intra-cycle variations exist. The variation in amplitude of the AP and SI motion trajectories can be determined from the lengths of the minor and major axes of the fitted ellipse (see FIG. 7B). Motion of the centroid of the fitted ellipse and the correlation of the AP and SI motion trajectories of the $m_{ext}3$ and $m_{int}5$ is provided by the rotation of the ellipse in different cycles (see FIGS. 7A and 7B) that characterize base line shifts and the average position of the markers.

Figure 9A:
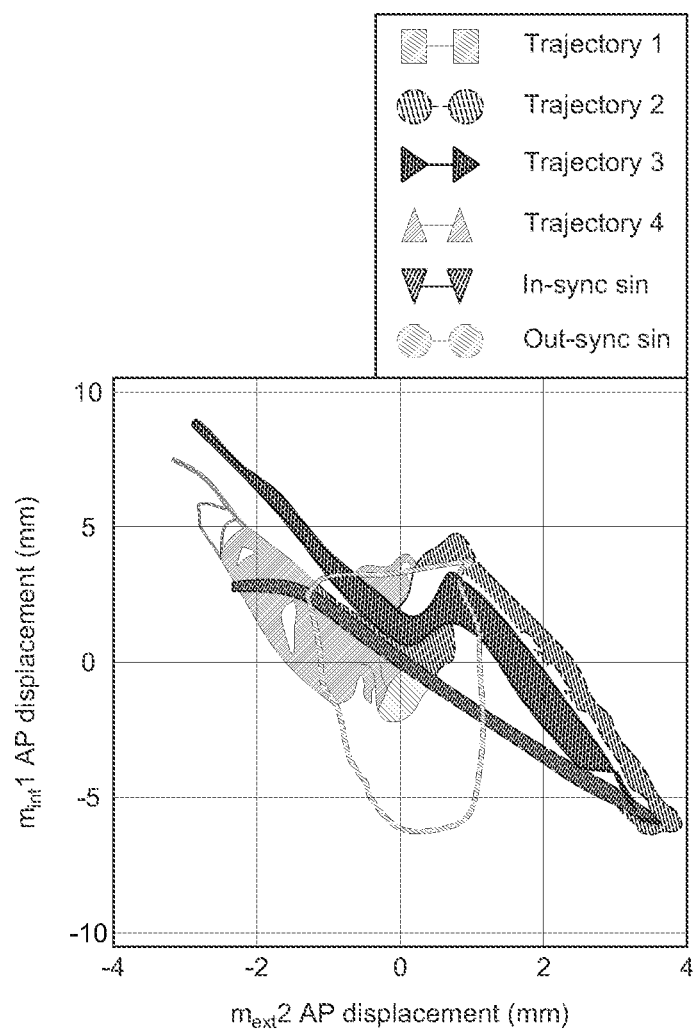
FIG. 9A is a set of graphs showing the change in the correlation of AP displacement of an external marker ($m_{ext}2$) and AP displacement of an internal marker ($m_{int}10$) for 6 exemplary trajectories.
Figure 9B:
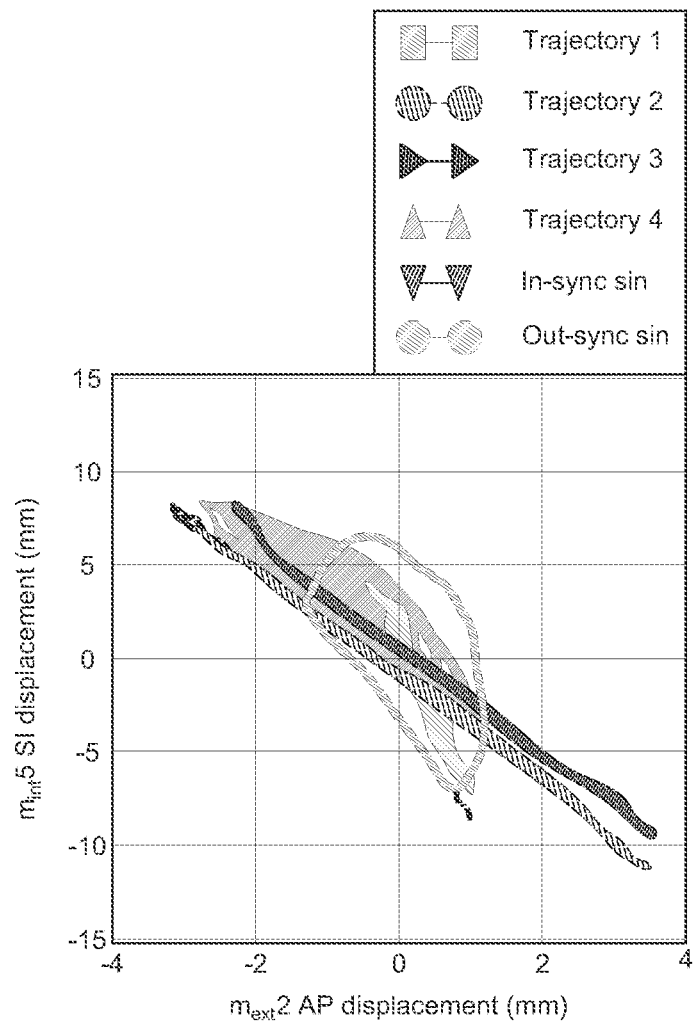
FIG. 9B is a set of graphs showing the change in the correlation of AP displacement of an external marker ($m_{ext}2$) and SI displacement of an internal marker ($m_{int}5$) for 6 exemplary trajectories.

Variable Internal Correlation and Hysteresis:

As noted above, FIG. 8 is a sagittal fluoroscopic image of the anthropomorphic lung motion phantom device of FIGS. 1A and 1B. FIG. 9A is a set of graphs showing the change in the correlation of AP displacement of an external marker ($m_{ext}2$) and AP displacement of an internal marker ($m_{int}10$) for six (6) exemplary trajectories. FIG. 9B is a set of graphs showing the change in the correlation of AP displacement of an external marker ($m_{ext}2$) and SI displacement of an internal marker ($m_{int}5$) for six (6) exemplary trajectories;

The deformable nature of the interior of the phantom can be observed from FIGS. 9A and 9B, where the correlations of AP and SI displacement of four internal markers are plotted. The correlation of the SI and AP displacement and the range of motion for each marker are different. For markers 5 and 7 ($m_{int}5$ and $m_{int}7$), the motion is primarily in the SI direction as they are not in the regions of the foam affected by the flexion of AP strips. For marker 10 ($m_{int}10$), the motion has a large AP component as the position of this marker is in close proximity to the AP strips. Motion of marker 8 ($m_{int}8$), is composed of both AP and SI displacement as this marker is affected by both actuators.

Moreover, FIGS. 9A and 9B illustrate a change in correlation of marker displacements in the phantom as the input trajectories change.

Figure 10A:
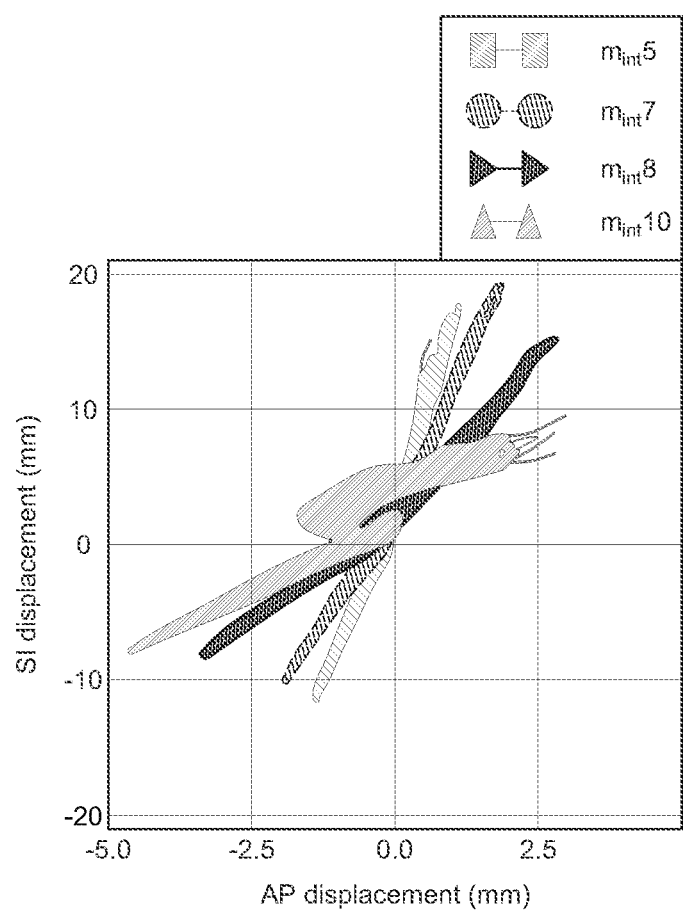
FIG. 10A is a set of graphs showing the change in the correlation of AP and SI displacement for four internal markers ($m_{int}5$, $m_{int}6$, $m_{int}7$, and $m_{int}9$) for a second trajectory.
Figure 10B:
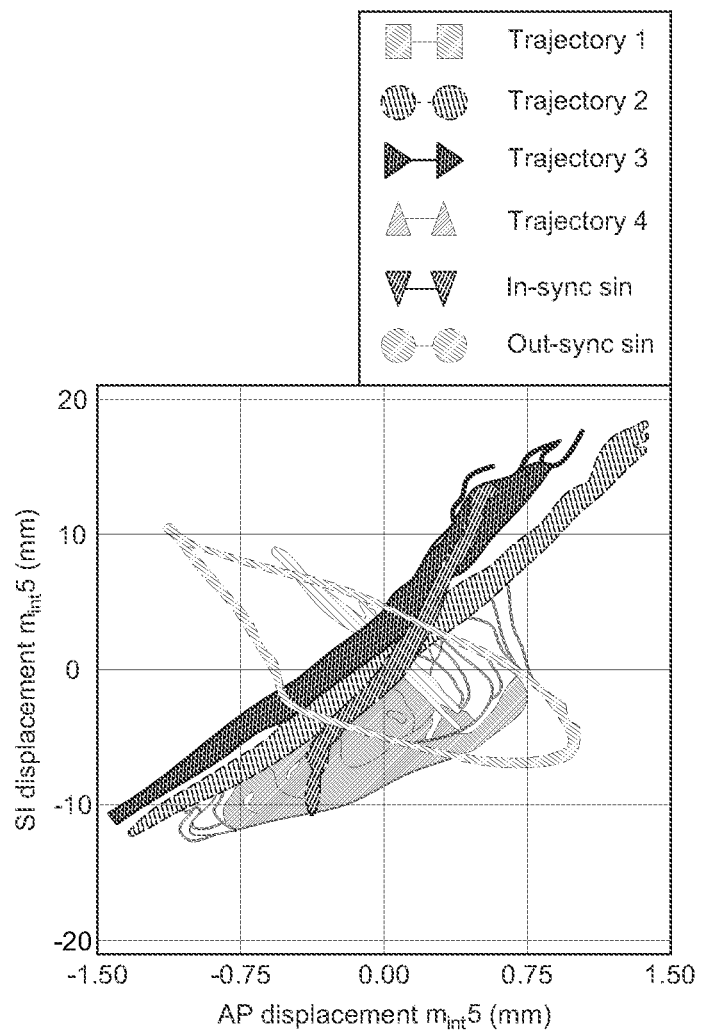
FIG. 10B is a set of graphs showing the change in the correlation of AP and SI displacement for a fifth internal marker ($m_{int}5$) for exemplary trajectories.

FIG. 10A shows the correlation of AP displacements of $m_{ext}2$ and $m_{int}10$ (closest marker to the AP flexible strips) for all trajectories. In a similar fashion, FIG. 10B shows the correlation of AP displacement of the same external marker ($m_{ext}2$) and SI displacement of $m_{int}5$, closest marker to the SI push plate, for exemplary input trajectories.

These results in the correlations above permit one to know how absolute position of a target site relative to an outside fixed reference moves/changes by measuring the external surface motion of a patient.

Example Applications

Quantifying the Error Due to Irregular Motion in 4DCT for Target Volume and Position Estimation:

Four-dimensional CT (4DCT) has become common in modern motion-managed thoracic scanning and radiotherapy. Using 4DCT, the respiratory cycle is typically sorted into 10 phases and then synced with the CT image acquisition process. The breathing trace is synchronized with the scan using the selected surrogate (by the vendor) and its measurement tools. Various methods and tools are available such as an air-bellows and belt (e.g., Philips), respiratory position management (e.g., Varian), or a respiratory belt.

However, many of these synchronization methods use movement of a point on external surface of the thorax as the breathing surrogate to sort the acquired images. The outcome of the 4DCT scans are typically 10 volumetric images (3-D image sets), each set being representative of the anatomical configuration of one phase in the respiratory cycle. For each set (3-D image), the sequential slices along the longitudinal axis composing the image are from a particular phase in the breathing cycle. The number of the slices depend on the thickness of each slice defined by the characterizations of the machine, the couch velocity, and the detector size. For instance, if the slice thickness is 3 mm and 7.5 cm of the lungs is necessary for viewing, the patient will receive 10 sets of 25 slices. The 3-D image of phase 0% is composed of all 25 slices from the first phase of the respiratory cycle, and the second volume is composed of slices categorized as belonging to the second phase of the respiration cycle and so on.

Thus, common 4DCT methods assume that the patient's breathing is regular. The sorting procedure is done for one cycle of respiration based on the amplitude or phase of the surrogate in that cycle, and the same sorting is applied to the rest of breathing cycles. As a result, the inter fraction and intra fraction change in the amplitude and the phase of breathing are not considered during the sorting procedure. So patients with irregular breathing, with drifts and fluctuations, are treated the same as ones with regular breathing. This causes artifact in the acquired images that are later used for treatment planning. Consequently, large margins are generally required to encompass motion, resulting in increased radiation dose to normal tissue. The consequence of such assumption has been studied by different groups to attempt to quantify associated errors. Yamamoto (noted above) has reported in a statistical study that neglecting such irregularities results in at least one artifact other than blurring in 90% of the 4DCT scans. Similarly, Person et al. (see above) have shown that in 85% lung cancer patients, the breathing irregularities are responsible for considerable discrepancies in gross tumor volume (GTV); in their next study Person et al. report that the size of the delineated GTV is affected by the scanning technique that is used for RT planning, whether it be the 4DCT gated scan or breath hold scans for peripheral lung tumor patients.

Such applications of patient data offer attractive strategies, with a directly applicable clinical perspective, for studying the effect of inter-cycle variations in breathing motion on the obtained 4DCT images. However, limitations on the availability of data and inherent complications associated with use of patient data and the complicated motions including translation, rotation, and deformation of organs as the body moves make the quantification of uncertainties from motion variability difficult. Simulation studies and virtual phantoms are some methods to avoid the patient data and its limitations, that make the study of motion variability across large scales of data possible. However, such methods suffer from a fundamental limitation for validation as none of their results can be empirically tested. Phantom measurements generally can address this problem. However, typical phantom designs do not provide external motion and have a constant internal-external correlation.

However, the phantom device according to one embodiment of this invention is configured to independently externally deform and internally deform. In addition, its motion is driven by two independently programmable actuators. This capability allows the user according to the practices of the present invention to reproducibly change the external to internal correlation of the deforming volume. Thus, the phantom device more closely approximates actual human anatomy undergoing respiration than typical phantom designs.

Effect of Variation in the Correlation of SI and AP Motion in Long Treatment

The importance of respiratory motion management is emphasized in the case of modern treatment planning methods such as Stereotactic Body Radiation Therapy (SBRT), proton, and heavy ion therapy methods. In conventional treatment planning, the target for the radiation is gross tumor volume (GTV) that is then expanded to internal tumor volume and planned tumor volume (PTV), respectively. In typical methods, the expansion from GTV to PTV has to be as small as possible since the patient receives a high dose of radiation in a few fractions for long durations of time. Some typical methods have attempted to reduce the volume that is being exposed by limiting motion of the patient, for example, by the patient using breath-hold (BH) or respiration belts. However the effectiveness of these methods is questionable due to the long duration of some of the treatments and also uncomfortable situation of the patients that may result in reverse effect and causing more movements. Furthermore, some methods attempt to quantify the motion (i.e. gating), track the motion, and move the radiation with the target, or by estimating the motion before it happens (e.g., using motion models). Validation of these methods is made possible by lung motion phantoms that simulate the respiratory motion.

Respiration causes the internal organs to have complicated motions including translation, rotation, and deformation. Different sets of muscles actuate the respiration and added to that is the sliding of different lobs of lung on each other and on the interior of the chest wall. Contribution of different factors to the respiration results in a varying correlation between the AP of the chest (up and down motion of the external chest wall) and SI of the internal torso anatomy. Tumor motion using typical 4DCT methods is generally assumed to be regular (e.g., constant internal and external correlation), and the AP motion of the surrogate is incorrectly generally assumed to be perfectly correlated with the internal anatomy motion in the SI direction throughout the entire treatment. The phantom device according to the practices of the present invention can be used for demonstration and measurement of the effect of variation in the motion on the accuracy of information estimated from 4DCT since the correlation between the AP displacement of external markers and SI displacement of the internal markers can be controlled.

Computer Implementation

Figure 11:
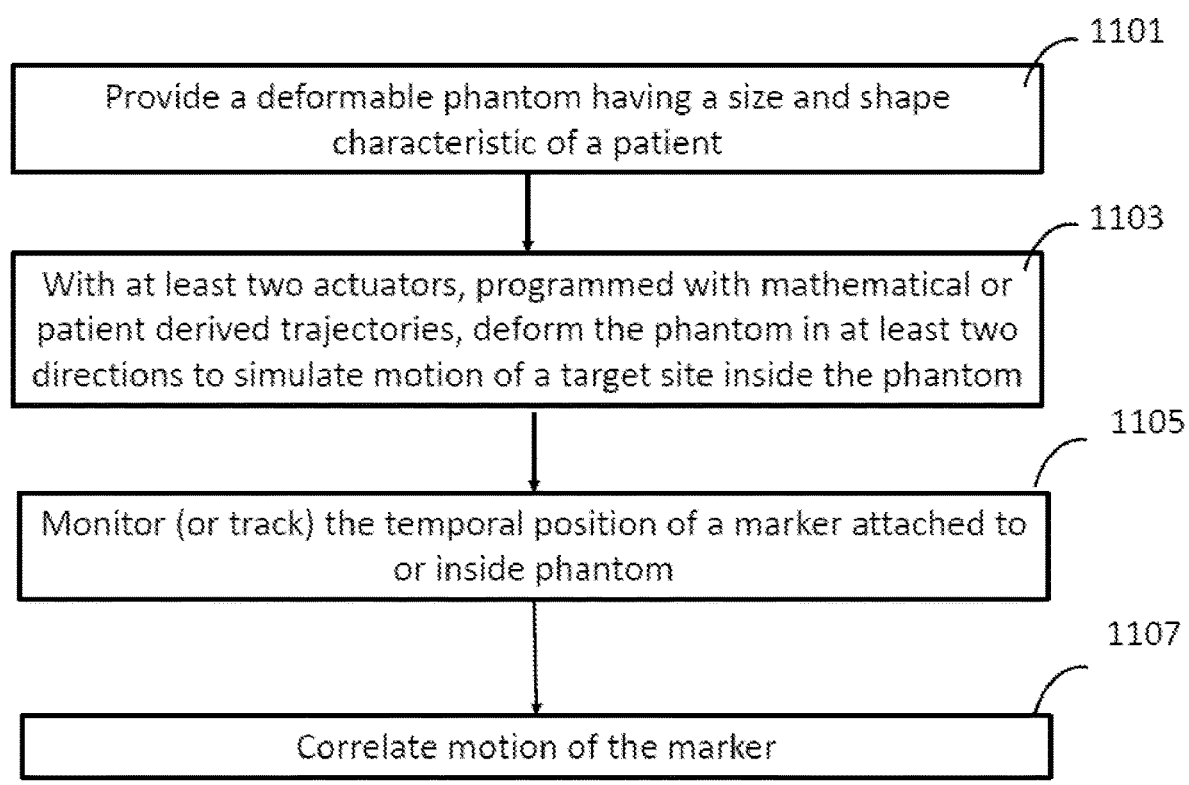
FIG. 11 is a flow chart depicting one method of the present invention for using the phantom device of FIGS. 1A and 1B.

FIG. 11 is a flow chart depicting one method of the present invention for using the phantom described above as part of computerized control of radiation protocols. Referring now to FIG. 11, what is shown is a series of steps for carrying out a method of predicting where a target site inside a patient moves in time.

At 1101, a deformable phantom is provided with a size and shape characteristic of a patient. At 1103, with at least two actuators, programmed with mathematical or patient recorded motion trajectories, deform the phantom in at least two directions to simulate motion of a target site inside the patient. At 1105, the temporal position of a marker attached to or inside the phantom is monitored (or tracked). At 1107, the motion of the marker is correlated. For example, with the simulated movement of the phantom, the motion of the marker can be correlated with the motion of other markers or landmarks that are placed or present internally within the phantom, or markers or landmarks that are placed or present on the external surface of the phantom. Thereafter, the correlation data can be exported to at least one of a CT for tomographic image correction or a LINAC for control of radiation exposure.

Figure 12:
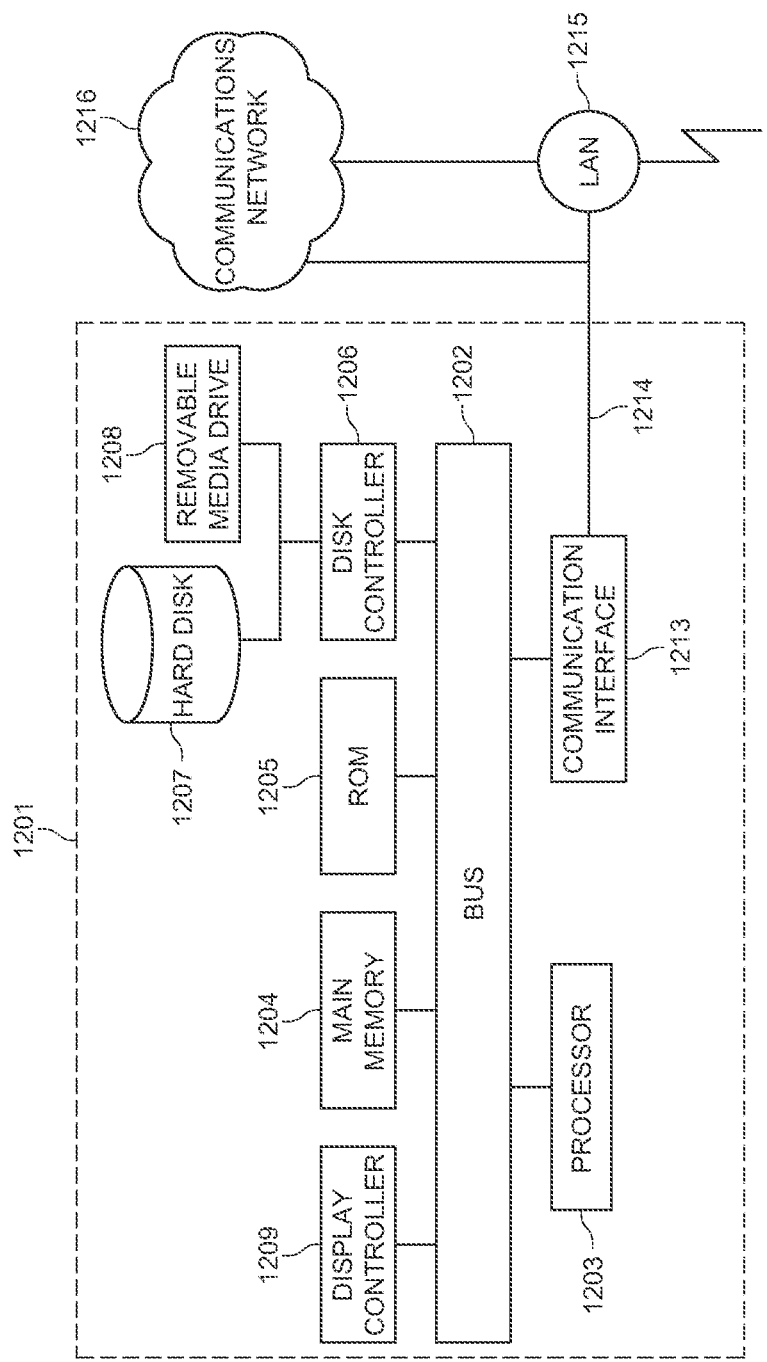
FIG. 12 is a computer system 1201 for implementing various embodiments of the invention.

FIG. 12 illustrates a computer system 1201 for implementing various embodiments of the invention. In particular, computer system 1201 may be used as control system 100 to perform any or all of the functions described above, including some or all of the steps described in FIG. 11. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable read only memory (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display, such as a cathode ray tube (CRT), for displaying information to a computer user. The computer system includes input devices, such as a keyboard and a pointing device, for interacting with a computer user and providing information to the processor 1203. The pointing device, for example, may be a mouse, a trackball, or a pointing stick for communicating direction information and command selections to the processor 1203 and for controlling cursor movement on the display to a user of the phantom device.

The computer system 1201 performs a portion or all of the processing steps of the invention (such as for example those described in relation to FIGS. 4A-7B, and 9A-11) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the invention includes software for controlling the computer system 1201, for driving a device or devices for implementing the invention, and for enabling the computer system 1201 to interact with a human user. Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the invention remotely into a dynamic memory and send the instructions. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213.

Numerous modifications and variations of the invention are possible in light of the above teachings. It is therefore to be understood that within the scope of the appended claims, the invention may be practiced otherwise than as specifically described herein.

The invention claimed is:

1. A lung motion phantom device comprising:
a body having an outer shell and a lung insert;
a first actuator connected to a first drive linkage for driving a first displacement of an internal volume of the lung insert and an outer surface of the outer shell in a first direction;
a second actuator connected to a second drive linkage for driving a second displacement of the internal volume of the lung insert and the outer surface of the outer shell in a second direction different than the first direction;
at least one bendable strip component inside the lung insert and configured to be driven by the second drive linkage to produce deflection of the at least one bendable strip component in the second direction;
a controller programmed to control the first and second actuators such that the first and second displacements simulate movement of an external surface and an interior of a thoracic region of a patient.

2. The device of claim 1, wherein the outer shell is a flexible shell, and the lung insert fills a volume formed by the outer shell.

3. The device of claim 1, wherein the body is externally and internally deformable by motions of the first drive linkage and the second drive linkage.

4. The device of claim 3, wherein:
the first drive linkage comprises a first push plate connected thereto,
the second drive linkage comprises a second push plate connected thereto, and
the at least one bendable strip component comprises at least one bending strip connected at a longitudinal end thereof to the second push plate, the bending strip under compression from the second push plate bending upward along the second direction,
the first push plate is configured to push against the lung insert in the first direction to thereby expand the lung insert, and
the second push plate is configured to push against the longitudinal end of the at least one bending strip to thereby displace the lung insert in the second direction.

5. The device of claim 4, wherein the bending strip comprises a variable-stiffness strip.

6. The device of claim 1, wherein the controller is programmed to independently change an amplitude or a frequency of the first and second displacements.

7. The device of claim 6, wherein the controller is programmed to operate the first and second actuators such that the first and second displacements follow sinusoidal rhythms.

8. The device of claim 7, wherein the sinusoidal rhythms of the first and second displacements are synchronized.

9. The device of claim 8, wherein the sinusoidal rhythms of the first and second displacements are at least one of in-phase or out of phase displacements.

10. The device of claim 7, wherein the sinusoidal rhythms of the first and second displacements have a variable phase correlation.

11. The device of claim 7, wherein the sinusoidal rhythms of the first and second displacements are not synchronized.

12. The device of claim 1, wherein the controller is programmed to operate the first and second actuators such that the first and second displacements comprise simultaneous displacements.

13. The device of claim 1, wherein the controller is programmed to operate the first actuator such that the first displacement comprises a superior-inferior displacement of the outer shell, and
wherein the controller is programmed to operate the second actuator such that the second displacement comprises an anterior-posterior displacement of the outer shell.

14. The device of claim 1, wherein the controller is programmed to operate the first and second actuators such that the first and second displacements cause motion of the outer shell of the body which simulates at least one of a respiratory motion trajectory and a patient-derived motion trajectory.

15. The device of claim 1, wherein the controller is programmed to operate the first and second actuators such that the first and second displacements produce an expansion of an outer surface area of the outer shell and a change in the internal volume of the lung insert.

16. The device of claim 15, wherein the controller is programmed to operate the first and second actuators based on user-input to change an internal-to-external correlation of the internal volume of the lung insert to the surface area of outer shell.

17. The device of claim 1, wherein the controller is programmed to operate the first and second actuators such that the first and second displacements cause the body motion to simulate human thoracic anatomy undergoing respiration.

18. The device of claim 1, further comprising plural radio-opaque fiducial markers comprising at least one external marker disposed on the external shell of the phantom and at least one internal marker disposed inside the lung insert.

19. The device of claim 18, wherein the controller is configured to receive and record data associated with temporal positions of the fiducial markers, and the controller is programmed to calculate from the data a correlation between a temporal position of the external marker and a temporal position of the internal marker.

20. A lung motion phantom device comprising:
a body having an outer shell and a lung insert;
a first actuator connected to a first drive linkage for driving a first displacement of an internal volume of the lung insert and an outer surface of the outer shell in a first translational direction which generates primarily superior-inferior (SI) motion of the outer surface of the outer shell;
a second actuator connected to a second drive linkage for driving a second displacement of the internal volume of the lung insert and the outer surface of the outer shell in a second translational direction different than the first translational direction, the second translational direction generates primarily anterior-posterior (AP) motion of the outer surface of the outer shell;
a controller programmed to control the first and second actuators such that the first and second displacements simulate movement of an external surface and an interior of a thoracic region of a patient.

* * * * *